(12) United States Patent
Solum et al.

(10) Patent No.: US 10,728,642 B2
(45) Date of Patent: Jul. 28, 2020

(54) PORTABLE CASE FOR MODULAR HEARING ASSISTANCE DEVICES

(71) Applicant: Starkey Laboratories, Inc., Eden Prairie, MN (US)

(72) Inventors: Jeffrey Paul Solum, Greenwood, MN (US); Yoshi Kasahara, Chaska, MN (US); Christopher D. Young, Shorewood, MN (US); Gregory John Haubrich, Champlin, MN (US); Preetham Varghese, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 16/135,784

(22) Filed: Sep. 19, 2018

(65) Prior Publication Data

US 2019/0268703 A1    Aug. 29, 2019

Related U.S. Application Data

(60) Provisional application No. 62/636,551, filed on Feb. 28, 2018.

(51) Int. Cl.
*H04R 1/02* (2006.01)
*H04R 1/10* (2006.01)
(Continued)

(52) U.S. Cl.
CPC .......... *H04R 1/028* (2013.01); *A61B 5/0022* (2013.01); *A61B 5/6815* (2013.01);
(Continued)

(58) Field of Classification Search
CPC .... H04R 1/028; H04R 1/1016; H04R 1/1025; H04R 25/30; H04R 25/505; H04R 25/554;
(Continued)

(56) References Cited

U.S. PATENT DOCUMENTS 5,204,917 A    4/1993   Arndt
5,253,300 A   10/1993   Knapp
(Continued)

FOREIGN PATENT DOCUMENTS

DE          8804743 U1    9/1989
DE     102009033898 B3   11/2010
(Continued)

OTHER PUBLICATIONS

International Search Report and Written Opinion of International Application No. PCT/US2019/019653, dated May 3, 2019, 13 pp.
(Continued)

*Primary Examiner* — Sean H Nguyen
(74) *Attorney, Agent, or Firm* — Mueting Raasch Group

(57) ABSTRACT

A portable case for storing hearing assistance devices is described that includes at least one retention structure configured to retain at least part of a hearing assistance device, one or more communication units configured to exchange information between the portable case and one or more external devices, and at least one processor. The processor is configured to: detect when the at least one retention structure shares an electrical connection with the at least part of the hearing assistance device that is retained by the at least one retention structure; and responsive to receiving data, from the hearing assistance device, via the electrical connection, while the at least part of the hearing assistance device is retained by the at least one retention structure, cause the one or more communication units to communicate with exchange the information data between the portable case and the one or more external devices.

24 Claims, 21 Drawing Sheets

(51) Int. Cl.
  *H02J 50/10* (2016.01)
  *H02J 7/00* (2006.01)
  *H04R 25/00* (2006.01)
  *G16H 40/63* (2018.01)
  *A61B 5/00* (2006.01)
  *G16H 40/67* (2018.01)
  *G16H 50/20* (2018.01)
  *H02J 7/10* (2006.01)

(52) U.S. Cl.
  CPC ........... *A61B 5/6817* (2013.01); *G16H 40/63* (2018.01); *G16H 40/67* (2018.01); *G16H 50/20* (2018.01); *H02J 7/0077* (2013.01); *H02J 50/10* (2016.02); *H04R 1/1016* (2013.01); *H04R 1/1025* (2013.01); *H04R 25/30* (2013.01); *H04R 25/505* (2013.01); *H04R 25/55* (2013.01); *H04R 25/554* (2013.01); *H04R 25/65* (2013.01); *A61B 2560/0456* (2013.01); *H02J 2007/10* (2013.01); *H04R 25/558* (2013.01); *H04R 25/602* (2013.01); *H04R 2225/021* (2013.01); *H04R 2225/023* (2013.01); *H04R 2225/025* (2013.01); *H04R 2225/31* (2013.01); *H04R 2225/55* (2013.01); *H04R 2225/61* (2013.01); *H04R 2460/03* (2013.01); *H04R 2460/17* (2013.01)

(58) Field of Classification Search
  CPC .............. H04R 25/65; H04R 2225/021; H04R 2225/025; H04R 2463/03; H04R 2460/17; H02J 50/10; H02J 7/0077; H02J 2007/10
  USPC ........................................................ 381/323
  See application file for complete search history.

(56) References Cited

U.S. PATENT DOCUMENTS

| | | |
|---|---|---|
| 5,565,759 A | 10/1996 | Dunstan |
| 7,106,877 B1 | 9/2006 | Linville |
| 7,110,562 B1 | 9/2006 | Feeley et al. |
| 7,151,839 B2 | 12/2006 | Niederdrank |
| 8,169,938 B2 | 5/2012 | Duchscher et al. |
| 9,543,778 B1 | 1/2017 | Corti |
| 2009/0262964 A1 | 10/2009 | Havenith et al. |
| 2012/0041517 A1 | 2/2012 | Walsh et al. |
| 2012/0140963 A1 | 6/2012 | Larsen et al. |
| 2013/0294627 A1 | 11/2013 | Karlsen |
| 2013/0034584 A1 | 12/2013 | Bennett et al. |
| 2013/0343584 A1 | 12/2013 | Bennett et al. |
| 2013/0343585 A1 | 12/2013 | Bennett et al. |
| 2014/0156775 A1 | 6/2014 | Payne et al. |
| 2014/0254845 A1 | 9/2014 | Hastrup |
| 2015/0036835 A1* | 2/2015 | Chen ............... H04R 1/1041 381/74 |
| 2015/0181357 A1 | 6/2015 | Krystek et al. |
| 2015/0341730 A1 | 11/2015 | Pedersen et al. |
| 2015/0350797 A1 | 12/2015 | Müller |
| 2016/0006292 A1 | 1/2016 | Hatanaka et al. |
| 2016/0058093 A1 | 3/2016 | Kennard et al. |
| 2016/0100261 A1 | 4/2016 | Shennib |
| 2017/0064429 A1 | 3/2017 | Hirsch et al. |
| 2017/0094390 A1 | 3/2017 | Chawan et al. |
| 2017/0180842 A1* | 6/2017 | Boesen ................ G10L 15/22 |
| 2017/0195804 A1 | 7/2017 | Sandhu et al. |
| 2017/0289711 A1 | 10/2017 | Maas |
| 2018/0014109 A1 | 1/2018 | Boesen |
| 2018/0020295 A1 | 1/2018 | Pander et al. |
| 2018/0027343 A1 | 1/2018 | Dobson et al. |
| 2018/0124491 A1 | 5/2018 | Dragicevic et al. |

FOREIGN PATENT DOCUMENTS

| | | |
|---|---|---|
| EP | 2849462 A1 | 3/2015 |
| EP | 3035710 A1 | 6/2016 |
| EP | 3101917 A1 | 12/2016 |

OTHER PUBLICATIONS

Invitation to Restrict or Pay Additional Fees, from International Application No. PCT/US2019/019649, dated May 3, 2019, 14 pp.
Invitation to Restrict or Pay Additional Fees, from International Application No. PCT/US2019/019657, dated Apr. 30, 2019, 11 pp.
Invitation to Restrict or Pay Additional Fees, from International Application No. PCT/US2019/019659, dated Apr. 29, 2019, 12 pp.
Office Action from U.S. Appl. No. 16/135,712, dated Jun. 27, 2019, 13 pp.
Office Action from U.S. Appl. No. 16/135,829, dated Jul. 12, 2019, 14 pp.
International Search Report and Written Opinion of International Application No. PCT/US2019/019657, dated Jun. 26, 2019, 16 pp.
International Search Report and Written Opinion of International Application No. PCT/US2019/019659, dated Jun. 24, 2019, 18 pp.
Cho et al., "A 10.8 mW Body Channel Communications/MICS Dual-Band Transceiver for a Unified Body Sensor Network Controller," IEEE Journal of Solid-State Circuits, vol. 44, No. 12, Dec. 2009, pp. 3459-3468.
Hao et al., "Wireless body sensor networks for health-monitoring applications," Physiological Measurement, vol. 29, No. 11, Nov. 2008, 42 pp.
Majumder et al., "Wearable Sensors for Remote Health Monitoring," Sensors, vol. 1, No. 130, Jan. 12, 2017, 45 pp.
U.S. Appl. No. 16/289,078, filed Feb. 28, 2019, by Solum et al.
U.S. Appl. No. 16/135,712, filed Sep. 19, 2018, by Solum et al.
U.S. Appl. No. 16/135,829, filed Sep. 19, 2018, by Solum et al.
U.S. Appl. No. 16/135,867, filed Sep. 19, 2018, by Solum et al.
U.S. Appl. No. 16/230,024, filed Dec. 21, 2018, by Higgins et al.
Response to Office Action from U.S. Appl. No. 16/135,829, filed Oct. 11, 2019.
International Search Report and Written Opinion of International Application No. PCT/US2019/019649, dated Jul. 5, 2019, 19 pp.
Office Action from U.S. Appl. No. 16/135,867, dated Sep. 30, 2019, 15 pp.
Response to Office Action dated Jun. 27, 2019, from U.S. Appl. No. 16/135,712, 10 pp.
File History for U.S. Appl. No. 16/135,712.
File History for U.S. Appl. No. 16/135,829.
File History for U.S. Appl. No. 16/135,867.
File History for U.S. Appl. No. 16/289,078.

* cited by examiner

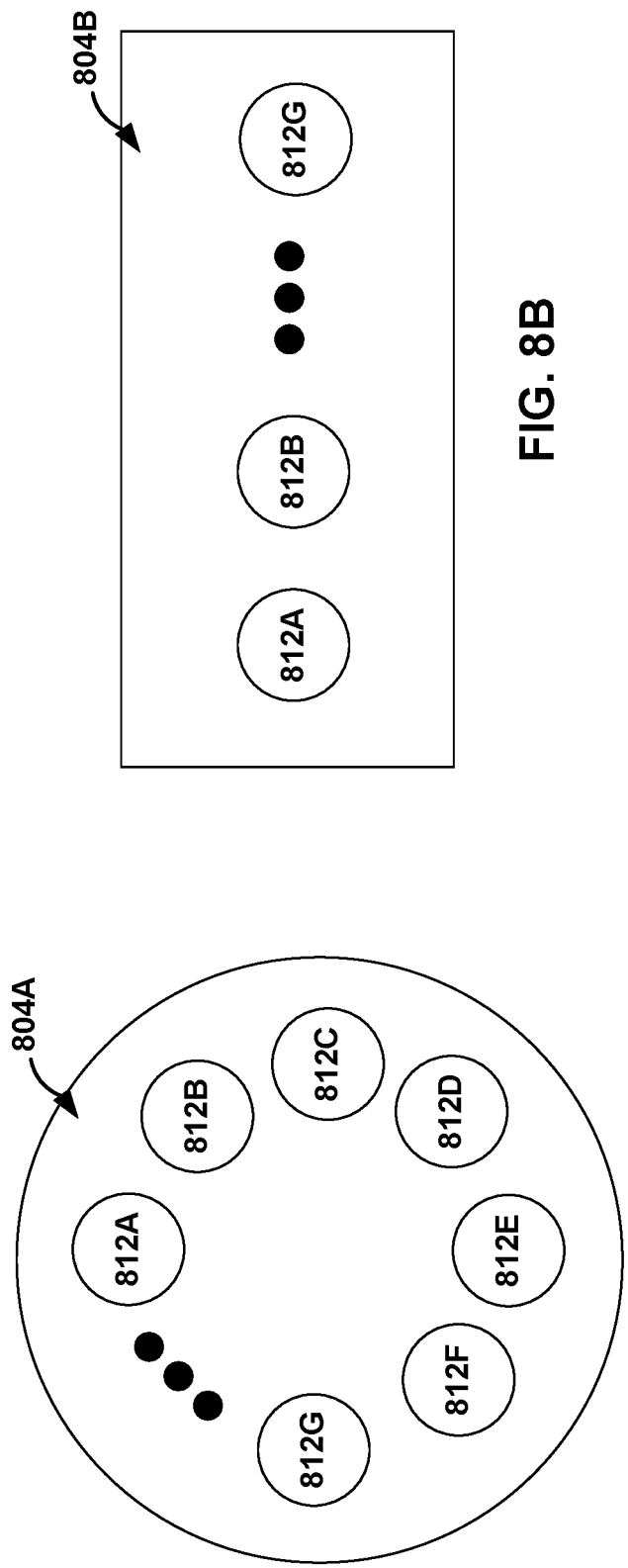

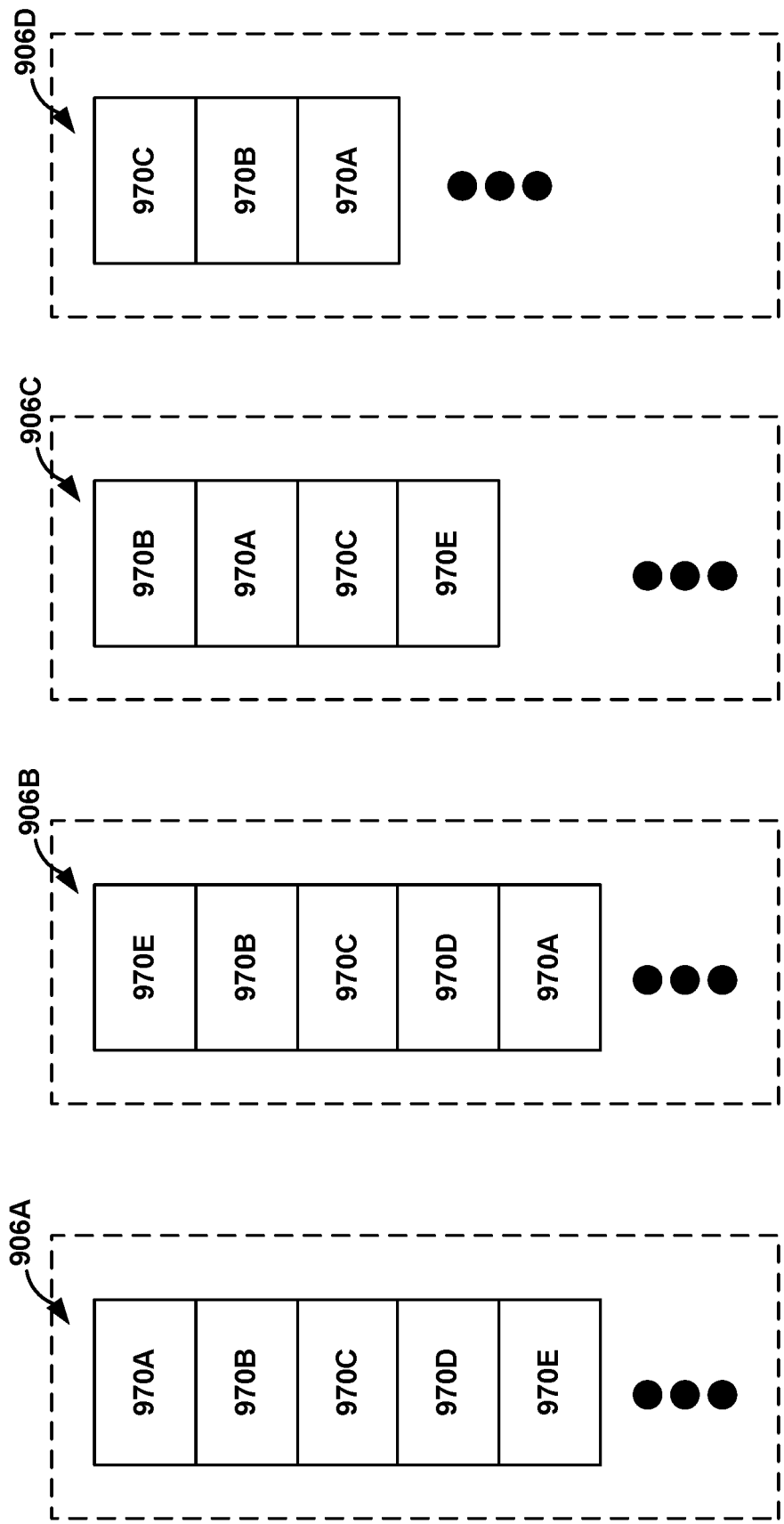

PORTABLE CASE FOR MODULAR HEARING ASSISTANCE DEVICES

This application claims the benefit of U.S. Provisional Application No. 62/636,551, filed Feb. 28, 2018, the entire content of which is hereby incorporated by reference.

TECHNICAL FIELD

This disclosure relates to hearing assistance devices such as hearing aids, wireless ear-buds, head-sets, and other devices for hearing sound.

BACKGROUND

Some hearing assistance devices (also commonly referred to as "hearing aids" and "hearing instruments") include additional features beyond just environmental sound-amplification. For example, some modern hearing assistance devices include advanced audio processing for improved device functionality, controlling and programming the devices, and beamforming, and some can even communicate wirelessly with external devices including other hearing aids (e.g., for streaming media). As hearing assistance devices perform more complex operations, their use can quickly deplete a typical, disposable power source (e.g., zinc-air primary-cell battery) or rechargeable power source, resulting in a user having to frequently dispose of, and replace and recharge, dead batteries.

Because hearing impaired users depend on their hearing assistance devices to perform essential life tasks, users may not be able to go without their hearing assistance devices in the case of a depleted power source. Furthermore, having to frequently swap out a depleted power source, particularly for someone with reduced finger dexterity, can be challenging and tedious.

SUMMARY

In one example, a portable case for storing hearing assistance devices includes at least one retention structure configured to retain at least part of a hearing assistance device, one or more communication units configured to exchange information between the portable case and one or more external devices, and at least one processor. The at least one processor is configured to: detect when the at least part of the hearing assistance device is retained by the at least one retention structure, and responsive to receiving data, from the hearing assistance device, via the electrical connection, cause the one or more communication units to communicate with the one or more external devices.

In another example, a method includes detecting, by a portable case for storing hearing assistance devices, when at least part of a hearing assistance device is retained by at least one retention structure of the portable case, and receiving, by the portable case, from the hearing assistance device, data. The method further includes, responsive to receiving the data while the at least part of the hearing assistance device is retained by the at least one retention structure, communicating, by the portable case, using one or more communication units of the portable case and based on the data, with one or more external devices.

In another example, a computer-readable storage medium includes instructions that, when executed by at least one processor of a portable case for storing hearing assistance devices, cause the at least one processor to: detect when at least part of a hearing assistance device is retained by at least one retention structure of the portable case, receive, from the hearing assistance device and while the at least part of the hearing assistance device is retained by the at least one retention structure, data, and responsive to receiving the data while the at least part of the hearing assistance device is retained by the at least one retention structure, communicate, using one or more communication units of the portable cases and based on the data, with one or more external devices.

The details of one or more aspects of the disclosure are set forth in the accompanying drawings and the description below. Other features, objects, and advantages of the techniques described in this disclosure will be apparent from the description, drawings, and claims.

BRIEF DESCRIPTION OF DRAWINGS

FIGS. 8A through 8C are conceptual diagrams illustrating some example retention structure arrangements of a portable case for storing and charging behind-ear portions of an example hearing assistance device, in accordance with one or more aspects of the present disclosure.

FIGS. 9A through 9D are conceptual diagrams illustrating example behind-ear portions of an example hearing assistance device, in accordance with one or more aspects of the present disclosure.

DETAILED DESCRIPTION

In one example, this disclosure relates to a modular hearing assistance device (also referred to herein as a "hearing aid" or "hearing instruments") that relies on a combination of one or more behind-ear portions configured as rechargeable power sources that may also provide additional device functionality. In addition, the disclosure describes examples of a portable case that may store the behind-ear portions, charge the behind-ear portions that are configured as rechargeable power sources, and/or perform other tasks on behalf of the hearing assistance device and a user. The described hearing assistance device may have, in some examples, attachment features that enable the behind-ear portions to quickly and easily attach or detach to in-ear components of the hearing assistance device, for example, to swap out a depleted power source, or to tailor the hearing assistance device for a particular situation. These features may eliminate some of the difficulty users have in replacing traditional power sources. In some examples, similar attachment features of the portable case also may enable the behind-ear portions to quickly and easily detach or attach to charging retention structures of the portable case, also in a way that is user friendly.

In this way, the described modular hearing assistance device and portable case may together provide a seemingly endless, and more reliable, user experience. In some examples, the modular hearing assistance device can be customized by a user by simply swapping out one type of behind-ear portion for a different type of behind-ear portion. In an example in which the portable case contains a supply of easily-swappable and recharged power sources, a user can enjoy all the advanced features provided by a sophisticated hearing assistance device, without worrying about running out of power. In addition, in some examples, the attachment features of the hearing assistance device and portable case may be configured to greatly reduce the frustration and anxiety experienced by some users from having to frequently swap out a traditional power source.

Although described primarily from the perspective of hearing assistance devices or hearing assistance systems, the described techniques are applicable to other types of "hearables". For example, the described techniques are applicable to a hearing assistance device, a hearing instrument, a hearing device, a hearing aid, a personal sound amplification product (PSAP), a headphone set, an earbud, a wireless ear-bud, or other hearing instrument that provides sound to a user for hearing.

Figure 1:
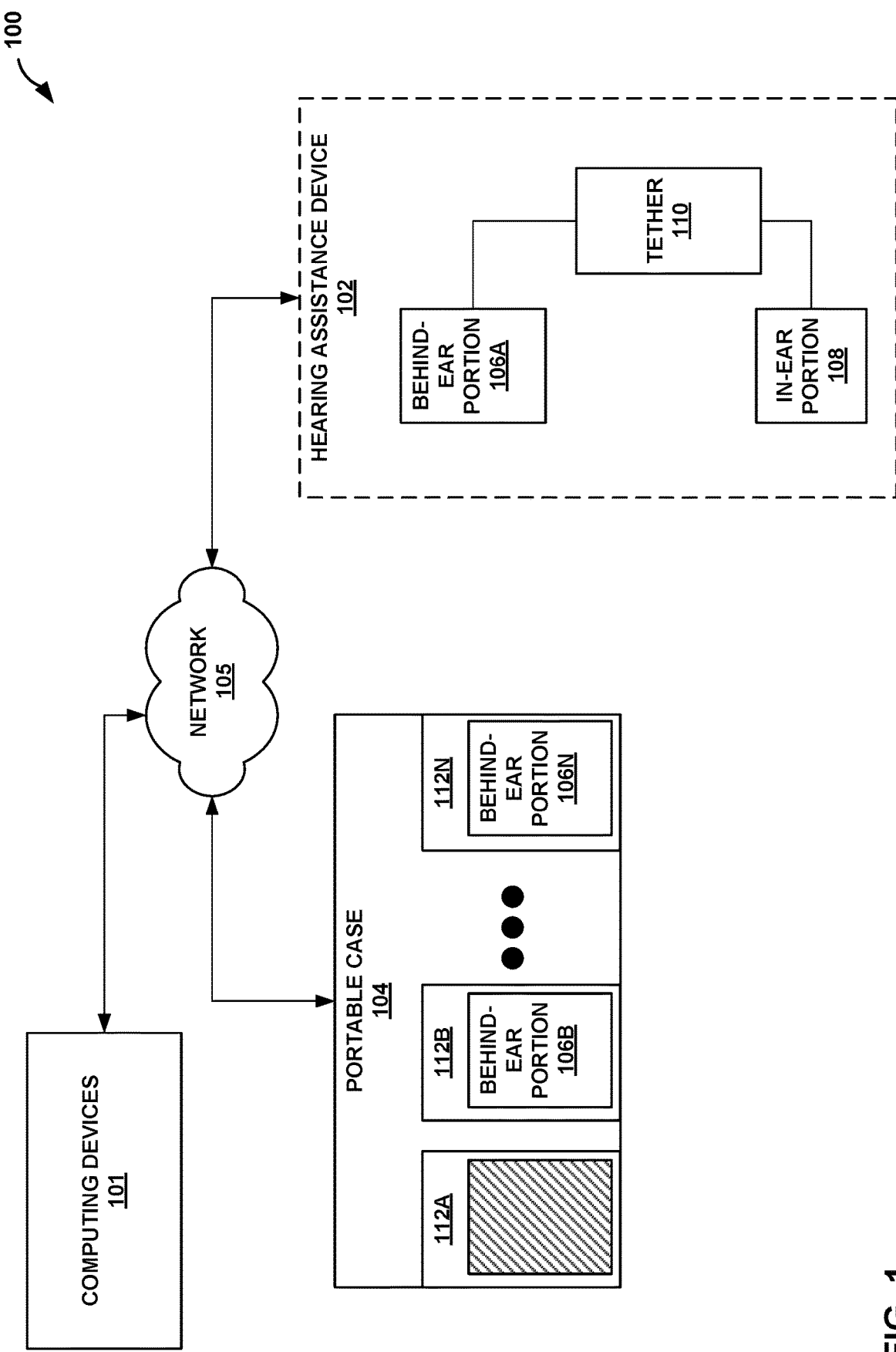
FIG. 1 is a block diagram illustrating an example hearing assistance system, in accordance with one or more aspects of the present disclosure.

FIG. 1 is a block diagram illustrating an example hearing assistance system, in accordance with one or more aspects of the present disclosure. System 100 of FIG. 1 includes hearing assistance device (HAD) 102 communicatively coupled via network 105 to portable case 104 and one or more computing devices 101. It should be understood that system 100 is only one example of a hearing assistance system according to the described techniques. System 100 may include additional or fewer components than those shown in FIG. 1.

Computing devices 101 may include a single electronic computing device or combination of two or more electronic computing devices, and may include: a hearing assistance device programmer (e.g., a device used by a medical professional to calibrate, change parameters, or otherwise configure HAD 102 and/or portable case 104 according to a treatment plan or treatment protocol), one or more mobile computing devices (e.g., a mobile phone, laptop computer, tablet computer, automobile computer, or other mobile device), one or more wearable computing devices (e.g., a computerized watch, computerized glasses, and the like), one or more server devices, one or more server blades, one or more personal computers, one or more content delivery network devices, and any other types of mobile, non-mobile, or wearable computing devices. Thus, in general, descriptions in this disclosure of computing devices 101 performing particular actions may be interpreted as some combination of one or more mobile, non-mobile, or wearable computing devices performing the particular actions.

Network 105 represents any public or private communications network, for transmitting data between computing systems and computing devices. For example, HAD 102, portable case 104, and computing devices 101 may communicate with each other via network 105. Computing devices 101, HAD 102, and portable case 104 may exchange data across network 105 using any suitable communication techniques. Network 105 may include a cellular communication network, such as a 3G network, 4G LTE network, a 5G network, or other cellular communication network using another type of wireless communication technology. Network 105 may include a short-range communication network, such as Bluetooth®, Wi-Fi®, or other type of communication network including direct-connections, such as Wi-Fi® direct and inferred direct communication networks. Network 105 may include or be communicatively coupled to the Internet or other types of networks, both personal and private. Network 105 may include one or more network hubs, network switches, network routers, or any other network equipment, that are operatively inter-coupled thereby providing for the exchange of information between components of system 100. Computing devices 101, HAD 102, and portable case 104 may each be operatively coupled to network 105 using respective network links. The links coupling computing devices 101, HAD 102, and portable case 104 to network 105 may be Ethernet or other types of network connections; such connections may be wireless and/or wired connections.

HAD 102 is primarily configured to provide sound to a user for hearing. As the term is used herein, a hearing assistance device, a hearing device, and a hearing instrument may each be a hearing aid, a personal sound amplification product (PSAP), a headphone set, a hearable, an earbud, a wireless ear-bud, or other hearing instrument that provides sound to a user for hearing. A single HAD 102 may be worn by a user with unilateral hearing loss. In the case of a user with bilateral hearing loss, two hearing instruments, such as HAD 102, are worn by the user, with one instrument in each ear.

While similar to other types of hearing instruments in that they each provide sounds to a user for hearing, a hearing assistance device, a hearing device, and a hearing instrument are specifically tailored to provide sounds to the user that help him or her overcome a hearing impairment. That is, a hearing assistance device, a hearing device, and a hearing instrument may have different configurations for different listening environments, or perform real-time speech detection and/or enhancement, as an alternative, or in addition, to providing other hearing capabilities (e.g., for listening to music) that do not specifically address a hearing impairment.

In general, there are three types of hearing assistance devices. A first type of hearing instrument includes a housing or shell that is designed to be worn in the ear for both aesthetic and functional reasons and enclose the electronic components of the hearing instrument. Such devices may be referred to as in-the-ear (ITE), in-the-canal (ITC), completely-in-the-canal (CIC), or invisible-in-the-canal (IIC) hearing instruments. Some in-the-ear hearing instruments have limited capabilities due to their small size and limited volume for housing electronics and power sources. Examples of drawbacks of IIC devices include a shortened battery life, lower fit rates due to the volume of components to be placed in the canal, lack of wireless features like programming and audio streaming, no telecoil, and patient frustration with changing batteries.

A second type of hearing instrument, referred to as a behind-the-ear (BTE) hearing instrument, includes a housing worn behind the ear contains all of the electronic components of the hearing instrument, including the receiver (i.e., the speaker). The receiver conducts sound to an earbud inside the ear via an audio tube.

Lastly, a third type of hearing instrument, referred to as a receiver-in-canal (MC) hearing instrument, has a housing worn behind the ear that contains all of the electronic components except for the receiver, which is worn in the ear canal. The output state of a RIC hearing instrument is electrically connected to the receiver worn in the ear canal.

Some traditional BTE and MC devices have limitations such as antenna and telecoil interference with radio circuitry, fixed battery life, fixed size and color, more limited microphone directionality than ITE devices, patient frustration with changing batteries, and inability to change-out rechargeable batteries. These traditional BTE and MC devices may also suffer from mechanical failures of battery doors, including: case gaps/ingress points, mechanical failure of the battery door part, poor detents making the off position hard to recognize, an open battery door causing the microphone cover to fall off, battery contact intermittency, and battery contact bending or breakage.

In the example of FIG. 1, HAD 102 is primarily configured as a MC hearing instrument and includes its electronic components distributed across three main portions: behind-ear portion 106A, in-ear portion 108, and tether 110. In operation, behind-ear portion 106A, in-ear portion 108, and tether 110 are physically and operatively coupled together to provide sound to a user for hearing. Behind-ear portion 106A and in-ear portion 108 may each be contained within a respective housing or shell. The housing or shell of behind-ear portion 106A allows a user to place behind-ear portion 106A behind his or her ear whereas the housing or shell of in-ear portion 108 is shaped to allow a user to insert in-ear portion 108 within his or her ear canal.

In-ear portion 108 is mainly used by HAD 102 for sound amplification and for outputting the amplified sound via an internal speaker (also referred to as a receiver) into a user's ear. That is, in-ear portion 108 receives sound waves from the environment and converts the sound into an input signal. In-ear portion 108 may amplify the input signal using a pre-amplifier, may sample the input signal, and may digitize the input signal using an analog-to-digital (A/D) converter to generate a digitized input signal. Audio signal processing circuitry of in-ear portion 108 may process the digitized input signal into an output signal (e.g., in a manner that compensates for a user's hearing deficit). In-ear portion 108 then drives an internal speaker to convert the output signal into an audio output.

Behind-ear portion 106A is a modular component of HAD 102 and is primarily configured to contain a rechargeable power source that provides electrical power, via tether 110, to in-ear portion 108. In some examples, in-ear portion 108 includes its own power source, and behind-ear portion 106A supplements the power source of in-ear portion 108.

Behind-ear portion 106A may include various other components, in addition to a rechargeable power source. For example, behind-ear portion 106A may include a radio or other communication unit to serve as a communication link or communication gateway between HAD 102 and the outside world. Such a radio may be a multi-mode radio or a software defined radio configured to communicate via various communication protocols. That is, behind-ear portion 106A may include communication components for communicating on network 105 on behalf of HAD 102 or for communicating directly with other hearing assistance devices. In addition to sometimes serving as a communication gateway, behind-ear portion 106A may perform various other advanced functions on behalf of HAD 102; such other functions are described below with respect to the additional FIGS.

Behind-ear portion 106A may be customizable. For example, behind-ear portion 106A may be made-up of one or more sub-portions that when mated together to form behind-ear portion 106A, perform the operations described herein with respect to behind-ear portion 106A. A user may mix and match different sub-portions to customize behind-ear portion 106A depending on the hearing needs of the user.

Behind-ear portion 106A may be similar or identical to any one of behind-ear portions 106B-106N that are shown in FIG. 1 being stored in portable case 104. In other words, a user may separate behind-ear portion 106A from tether 110 and exchange behind-ear portion 106A for any one of behind-ear portions 106B-106N. Behind-ear portions 106A-106N are referred to collectively as behind-ear portions 106.

Tether 110 forms one or more electrical links that operatively and communicatively couple behind-ear portion 106A to in-ear portion 108. Tether 110 may be configured to wrap from behind-ear portion 106A (e.g., when behind-ear portion 106A is positioned behind a user's ear) above, below, or around a user's ear, to inside-ear portion 108 (e.g., when inside-ear portion 108 is located inside the user's ear canal). When physically coupled to in-ear portion 108 and behind-ear portion 106A, tether 110 is configured to transmit electrical power from behind-ear portion 106A to in-ear portion 108. Tether 110 is further configured to exchange communication signals between portions 106A and 108. As described below with respect to the additional FIGS., tether 110 may act as a handle or carrying mechanism for a user to hold HAD 102 when the user of HAD 102 removes portions 106A and 108 from his or her body or when swapping out one behind-ear portion 106 for a different behind-ear portion 106.

Behind-ear portions 106 may include mechanical and/or magnetic attachment features that enable behind-ear portions 106 to quickly and easily couple or decouple with tether 110 and in-ear portion 108, for example, to swap out one of behind-ear portions 106 that has a depleted power source, for a different one of behind-ear portions 106 that has a charged power source. Small electrical connectors and tiny cables are replaced with mechanical and/or magnetic attachment features that may eliminate some of the difficulty users have in replacing traditional power sources, such as disposable batteries, used in other hearing assistance devices. In addition, similar mechanical and/or magnetic attachment features may also enable release or coupling of tether 110 and in-ear portion 108.

In addition to exchanging behind-ear portions 106 when a power source is depleted, a user may wish to swap one behind-ear portion 106 for another to customize or tailor HAD 102 for a particular situation. For instance, behind-ear portion 106A may include a Bluetooth radio for receiving a Bluetooth audio stream (e.g., being output by computing devices 101 or portable case 104) and behind-ear portion 106B may include, in place of the Bluetooth radio, a Wi-Fi radio for instead receiving information being transmitted over a Wi-Fi network. Other examples of radio technology may be used, for example, behind-ear portion 106A may include a cellular radio for transmitting and receiving telephony data and/or cellular data.

Portable case 104 is an example of a portable apparatus (e.g., meant to fit in a user's hand or pocket) which is used for storing and charging one or more modular, behind-ear portions of an example hearing assistance device, such as behind-ear portions 106 of HAD 102. In some examples, portable case may be configured to store and charge multiple behind-ear portions of an example hearing assistance device, such as behind-ear portions 106 of HAD 102. In addition, portable case 104 may provide additional advanced functionality to system 100, beyond just storing and charging power sources of behind-ear portions 106. For instance, other functions may include wired or wireless charging of the internal power source of portable case 104, remote control of hearing aid device HAD 102 (e.g., via controls on portable case 104), audio recording or wirelessly transmitting audio to HAD 102 via a remote microphone inside portable case 104, and facilitating wireless communication, via network 105, between portable case 104, computing devices 101, HAD 102, and other hearing assistance devices not shown.

Portable case 104 may come in a variety of different shapes and sizes that are suitable for carrying in a person's hand, securing to a person's body, or stowing in a clothes pocket or other secure location. In some examples, portable case 104 may be approximately four cubic inches or less, for instance, two inches wide by two inches tall, by three quarter inches deep, as one example. In some examples, portable case 104 may be greater than four cubic inches or less, for instance, three inches wide by two or three inches tall, by one inch deep, as one example. One dimension (i.e., height, width, or depth) could be decreased to accommodate an increase in another dimension to cause portable case 104 to have a different shape, without increasing volume or sacrificing portability. For instance, portable case 104 may be one and a half inches tall by one and a half inches wide by two inches deep, as one example. In other examples, portable case 104 may be spherical, cylindrical, conical, or have some other shape. For example, portable case 104 may be a four inch diameter disk shape that is a half inch thick.

In some cases, portable case 104 is configured to retain only behind-ear portions 106 of HAD 102 during storing and/or charging and not retain tether 110 and/or in-ear portion 108 during storing and charging. In this way, portable case 104 may conveniently provide a way for a user to swap out one behind-ear portion 106 for a different behind-ear portions 106 without having to swap out in-ear portion 108. Such a configuration may provide a more convenient user experience and also help ensure portable case 104 and behind-ear portions 106 (which do not enter a user's ear canal and are therefore less susceptible to contaminants from regular use) remain clean and sanitary. In addition, by retaining only behind-ear portions 106, the overall size of portable case 104 can be reduced by an amount proportional to a size of in-ear portion 108. In addition, in-ear portion 108 may be used by itself providing additional benefits. That is, hearing aid wearers sometimes feel stigmatized by having to wear a device which reveals their handicap. So it may be convenient for a wearer to sometimes remove behind-ear portions 106 to better conceal HAD 102 by only having to wear in-ear portion 108.

Of course, in other examples, portable case 104 is configured to retain all of HAD 102 during storing and/or charging. For example, portable case 104 may accommodate each of behind-ear portions 106, tether 110, and in-ear portion 108 simultaneously, for example, when a user is sleeping or traveling, portable case 204 may be configured to retain each part of HAD 102.

Portable case 104 may act as a radio for sending or receiving communications. Such a radio may be a multi-mode radio or a software defined radio configured to communicate via various communication protocols. Portable case 104 may act as an audio controller that scans for wireless audio broadcasts (e.g., AM/FM radio, Bluetooth, Wi-Fi, cellular, or other audio broadcasts) and may alert or otherwise output a notification to inform a user of potential audio sources (e.g., via audible, tactile, or visual alerts). Further, portable case 104 may provide the user a way to select a desired audio broadcast (e.g., using controls built into the case, hand gestures, or voice input). While portable case 104 may provide several advanced capabilities to system 100, portable case 104 may further enable HAD 102 to perform various advanced functions, for example, by offloading processing on behalf of HAD 102 to implement digital signal processing, speech recognition/language translation, artificial intelligence, or other advanced functions.

As shown in FIG. 1, portable case 104 includes one or more retention structures 112A-112N (collectively "retention structures 112"). Each of retention structures 112 is configured to retain an individual behind-ear portion of an example hearing assistance device, such as behind-ear portion 106A of HAD 102. For instance, retention structure 112B is shown storing behind-ear portion 106B and retention structure 112N is shown in FIG. 1 storing behind-ear portion 106N.

As used herein, the term "retention structure" refers to a cavity, a hole, an aperture, a recess, a groove, a slot, a space inside a retaining wall of a housing, or any other form of retention structure. In some examples, other features are included in a retention structure or other embodiments are possible. For example, the retention structure may be a retention area, or mounting area. In such an example, rather than insert behind ear portions 106 inside retention structures 112, behind-ear portions 106 may be inserted atop, or next to, retention structures 112. In other words, while described primarily as holding or retaining behind-ear portions 106, in some cases, retention structures 112 simply receive (but not necessarily tightly hold) behind-ear portions 106.

While a primary function of retention structures 112 may be storage individual behind-ear portions 106 when behind-ear portions 106 are not-in-use, each of retention structures 112 can also serve a dual purpose. For example, each of charging retention structures 112 may be configured to charge the rechargeable power source (e.g., a rechargeable battery) contained inside each of behind-ear portions 106. For example, charging circuitry of portable case 104 (not shown in FIG. 1) will charge the power source of behind-ear portion 106B when behind-ear portion 106B is placed inside retention structure 112B. Retention structures 112 may be mechanical components that receive one or more electrical connections (pins, pads, leafs, nodes, etc.) that contact corresponding electrical connections of behind-ear portion 106B. In some cases, no physical contact between the electrical connections of retention structures 112 and behind-ear portion 106B are necessary; retention structures 112 may instead be inductively coupled to behind-ear portion 106B for charging the power source or otherwise exchanging electrical signals.

Portable case 104 may include any quantity of retention structures 112. In some cases, portable case includes four retention structures 112 so that at least a first pair of HAD's 102 is always charged while a second pair is charging and a user is wearing a pair of HAD 102. In some cases, portable case includes two retention structures 112 for charging and storing a single pair of HADs 102. In other cases, portable case 104 includes three or more retention structures 112 for storing extra behind-ear portions 106.

Behind-ear portions 106 are designed to be user-friendly, particularly for someone with impaired finger dexterity or who struggles with changing batteries in traditional hearing aids. Behind-ear portions 106 may be designed such that, when depleted of electrical energy, a user does not need to remove the rechargeable power source from inside the housing of behind-ear portions 106 to charge the power source. A user may find that gripping a behind-ear portion 106 is easier than holding a traditional, hearing aid battery due to behind-ear portions 106 having a larger, more manageable size.

Rather, behind-ear portions 106 may each include one or more external contacts protruding through their external housing. The contacts of behind-ear portions 106 are configured to mate with a respective set of charging contacts located in any one of retention structures 112 when charging. The contacts of behind-ear portions 106 are also configured to mate with electrical terminals located at one end of tether 110 when being worn. The contacts may be exposed male bumps or plugs that mate into female sockets or the contacts may be exposed females sockets that mate over male bumps or plugs.

Each of retention structures 112 and behind-ear portions 106 may include mechanical and/or magnetic attachment features that improve the strength of a physical connection between behind-ear portions 106 and the charging circuitry of portable case 104 and the physical connection between behind-ear portions 106 and tether 110. These attachment features may eliminate some of the difficulty users have in replacing traditional power sources. The attachment features also ensure that a user cannot incorrectly seat behind-ear portions 106 inside retention structures 112. In some examples, the attachment features may further ensure that behind-ear portions 106 are correctly mated to tether 110.

FIGS. 2A through 2D are conceptual diagrams illustrating an example hearing assistance system, in accordance with one or more aspects of the present disclosure. FIGS. 2A through 2D are described in the context of system 100 of FIG. 1. For instance, portable case 204 of systems 200A and 200B are an example of portable case 104 of FIG. 1 and HAD 202, 202A, and 202B are each an example of HAD 102 of FIG. 1.

Figure 2A:
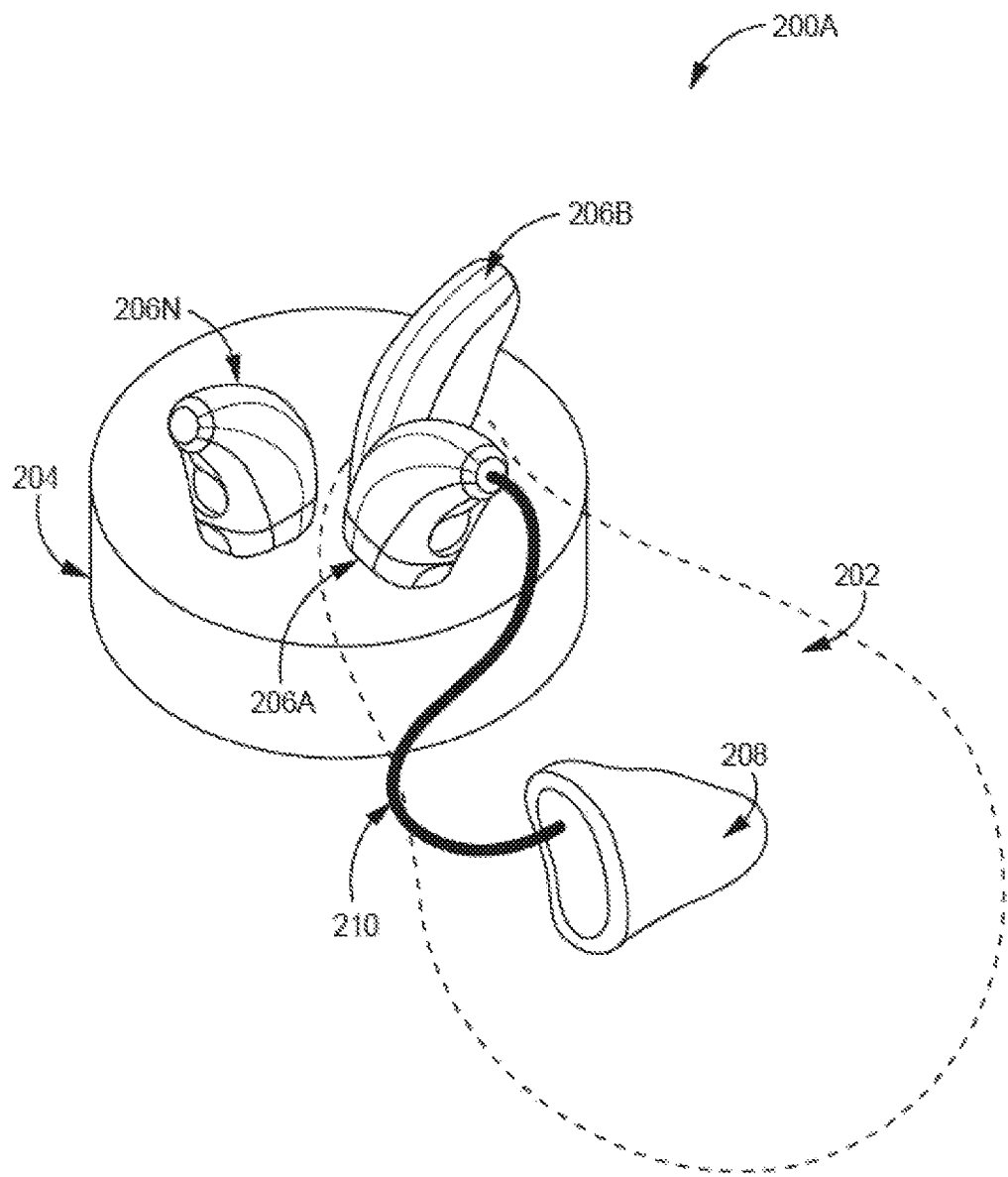
FIGS. 2A through 2D are conceptual diagrams illustrating an example hearing assistance system, in accordance with one or more aspects of the present disclosure.
Figure 2B:
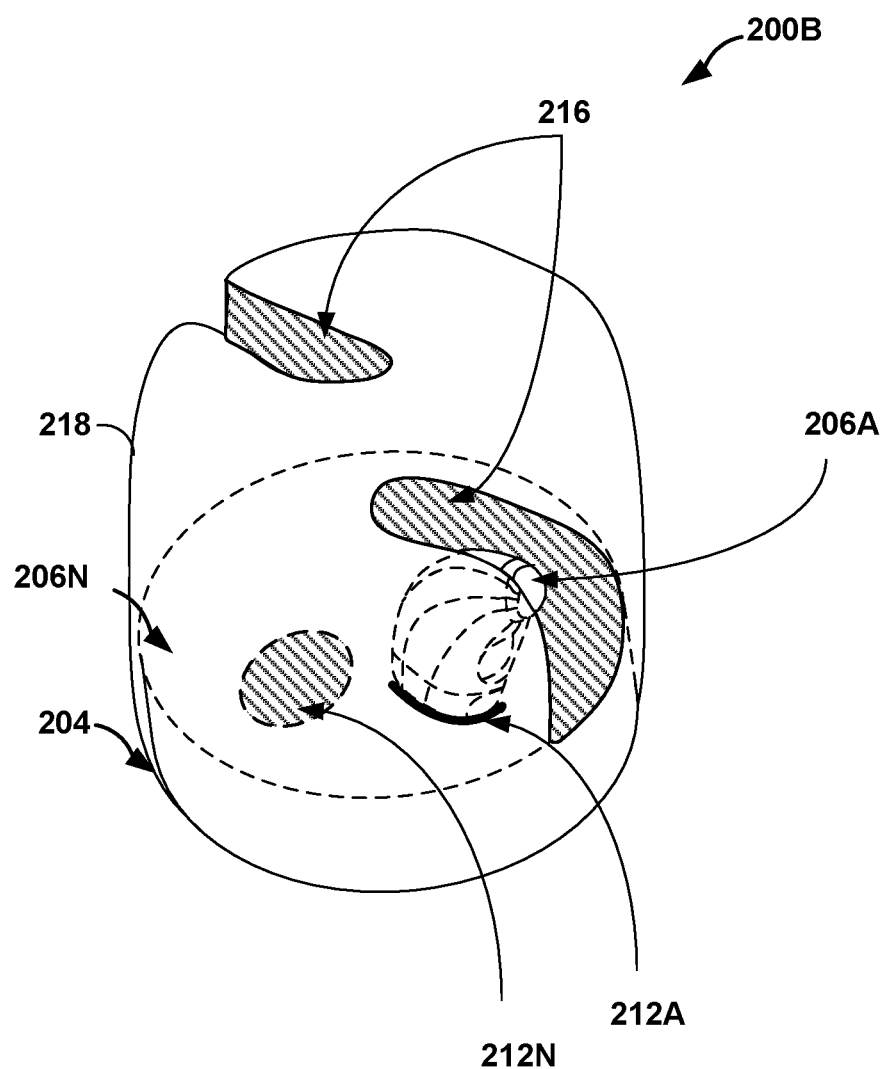
Figure 2C:
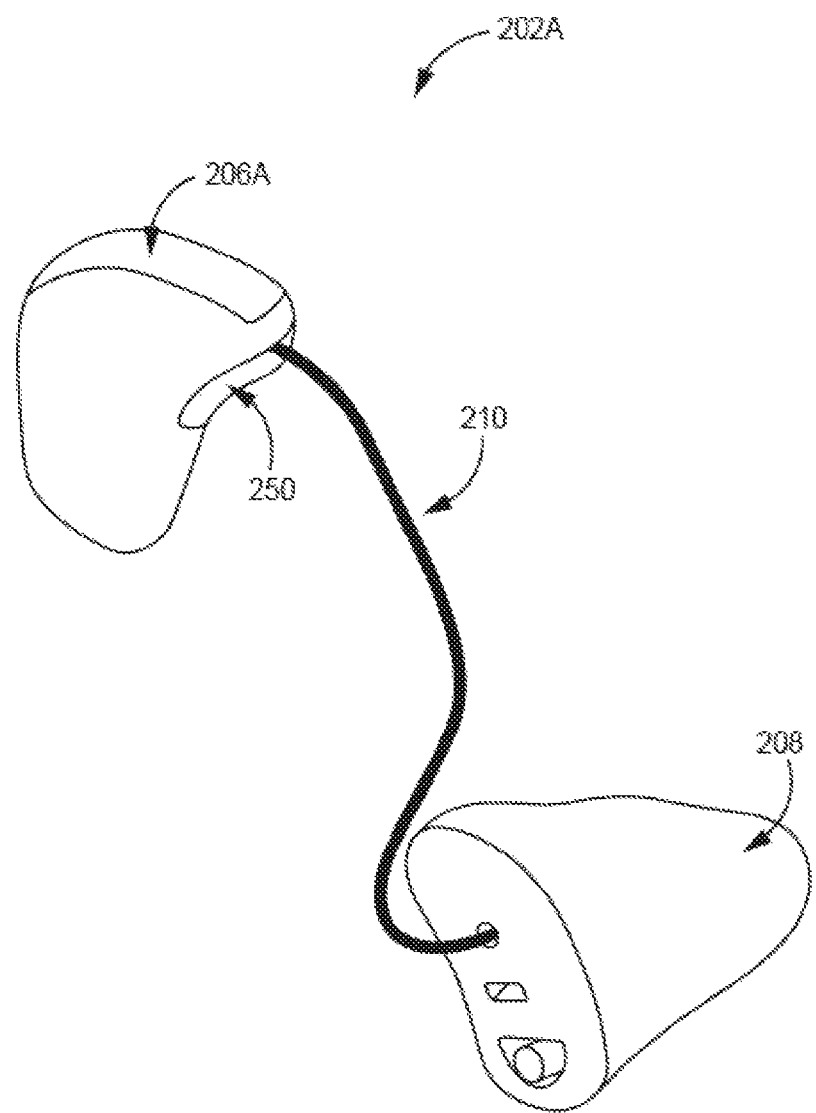
Figure 2D:
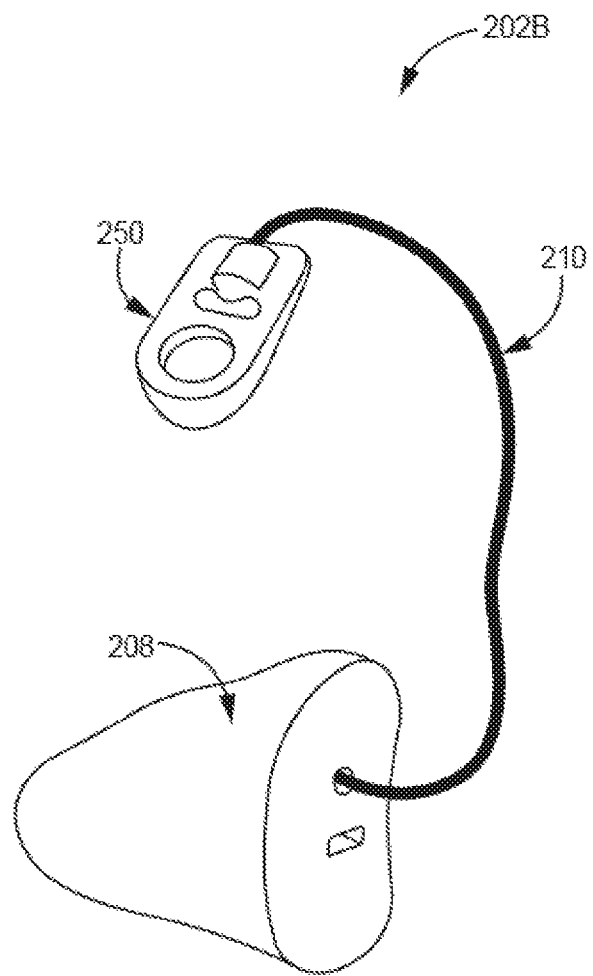

FIG. 2A shows an example of system 200A which includes portable case 204 and hearing assistance device 202 (referred to simply as "HAD 202"). FIG. 2B shows an example of system 200B, as an alternate view of system 200A, after tether 210 has been detached from behind-ear portion 206A. FIG. 2C shows HAD 202A as an example of HAD 200 from FIGS. 2A and 2B. HAD 202A includes behind-ear portion 206A, tether 210, and in-ear portion 208. FIG. 2D shows HAD 202B as an example of HAD 200 from FIGS. 2A and 2B. HAD 202B omits behind-ear portion 206A and includes only tether 210 and in-ear portion 208.

In the example of FIG. 2A, HAD 202 includes behind-ear portion 206A coupled to in-ear portion 208 via tether 210. Behind-ear portion 206A of HAD 202 is housed in a retention structure of portable case 204, for example, either to be subsequently detached from tether 210 for charging, or to be removed from portable case 204 via tether 210 to be worn by a user. In addition to storing (and in some instances charging) behind-ear portion 206A, portable case 204 also may charge one or more other behind ear portions. For example, in FIG. 2A, portable case 204 is also shown storing and/or charging behind ear portions 206B and 206N.

In FIG. 2B, tether 210 and in-ear portion 208 have been detached from behind-ear portion 206A. With tether 210 and in-ear portion 208 removed, FIG. 2B clearly shows openings 216 in cover 218 of portable case 204, which are included in cover 218 to enable insertion and removal of behind-ear portions 206A, B, and N. Also identified in FIG. 2B are retention structures 212A and 212N; each of retention structures 212A and 212N is configured to retain one of behind-ear portions 206. As one example, retention structure 212N is empty and retention structure 212A includes behind-ear portion 206A.

In the examples of each of FIGS. 2A and 2B, portable case 204 is configured in a carousel arrangement to facilitate quick and easy exchange of one behind-ear portion 206 for a different behind-ear portion 206. In other examples, portable case 204 may be configured in a linear or other such arrangement.

A user may manipulate cover 218 of portable case 204 to expose, via openings 216, an individual retention structure 212 or multiple retention structures 212 at a time (e.g., to retrieve a pair of behind-ear portions 206). For example, a user may manipulate cover 218 to expose, via one of openings 216, retention structure 212A (which is empty at the time). Next, the user may insert behind-ear portion 206A into retention structure 212A and detach behind-ear portion 206A from tether 210. The user may then manipulate cover 218 to cover retention structure 212A and expose, via one of openings 216, retention structure 212N. Finally, the user may attach behind-ear portion 206N to tether 210 and remove behind-ear portion 206N from retention structure 212N.

Although primarily described as being a rotary type cover (e.g., similar to that which may be used for some types of fishing tackle containers such as rotary slip shot sinker containers), cover 218 may be a hinge type cover (e.g., similar to a typical dental floss container lid) configured to flip up and down to open and close. Alternatively, cover 218 may be configured to slide to open and close. Cover 218 may be configured to reveal two or more retention structures 212 at a time (e.g., via openings 216) so multiple behind-ear portions 206 could be changed without further manipulation of cover 218. Likewise, cover 218 may be configured to reveal a single one of retention structures 212 at a time or more than two retention structures 212 at a time.

FIG. 2C shows an example of HAD 202A which includes behind-ear portion 206A, tether 210, and in-ear portion 208. FIG. 2D shows an example of HAD 202B omitting behind-ear portion 206A and including only tether 210 and in-ear portion 208.

Various attachment features can be used to attach behind-ear portion 206A to portable case 204 and to attach behind-ear portion 206A to tether 210. The various attachment features may include mechanical and/or magnetic components that enable easy (e.g., one-handed) exchange of behind-ear portion 206A to and from portable case 204 and to and from tether 210.

For example, as shown in FIGS. 2C and 2D, tether 210 includes attachment feature 250 (also referred to as "coupling feature 250"). Attachment feature 250 includes is configured to mate with an attachment feature of behind-ear portion 206A. When detached from attachment feature 250, the attachment feature of behind-ear portion 206A is configured to mate with one of retention structures 212. Such attachment features may include mechanical and/or magnetic components that enable tether 210 and behind-ear portion 206A to maintain a strong physical bond when being worn, enable retention structures 212 and behind-ear portion 206A to maintain a strong physical bond when behind-ear portion 206A is charging. Such mechanical and/or magnetic attachment features may further enable behind-ear portion 206A to quickly disconnect from retention structures 212 and tether 210.

In some examples, a mechanical catch may prevent two parts from being detached without sufficient force for overcoming the mechanical catch. And, in the case of a magnetic feature, the attachment features may be a mechanically and/or magnetically self-aligning design. That is, to configure behind-ear portion 206A for use, a user may simply bring attachment feature 250 near an attachment area of behind-ear portion 206A and the magnetic attraction between attachment feature 250 and the attachment area of behind-ear portion 206A may force the two parts together and enable an electrical connection between the two parts. Similarly, to configure behind-ear portion 206A for storage or charging in portable case 204, a user may simply position the attachment area of behind-ear portion 206A above an empty one of retention structures 212, and the magnetic attraction between the empty retention structure 212 and the attachment area of behind-ear portion 206A may allow a user to simply drop behind-ear portion 206A into the empty retention structure 212 where the electrical contacts of behind-ear portion 206A may automatically align with the charging contacts of the empty one of retention structures 212.

In some cases, the mechanical and/or magnetic attachment features described above enable release of their bonds via rotation. That is, with both portable case 204, behind-ear portions 206, and attachment feature 250 of tether 210 having magnets or mechanical catches, the magnets and/or mechanical catches can be configured so that after two parts are physically mated together, a ninety-degree rotation of either part may cause the magnetic attraction to switch to magnetic repulsion or may cause the mechanical catch to be bypassed, thereby releasing one part from the other. For example, to remove behind-ear portion 206A from portable case 204, a user can simply turn either part, e.g., ninety degrees, to cause behind-ear portion 206A to pop out of case 204; to detach behind-ear portion 206A from tether 210, a user can simply turn either part, e.g., ninety degrees, to cause behind-ear portion 206A to separate from tether 210.

The attachment features described above may be improved via an electro-permanent magnetic catch. For example, portable case 204 may include circuitry to cause electro-permanent magnets in retention structure 212A to have a greater amount of magnetic attraction to behind-ear portion 206A when charging to prevent a user from separating the two parts prematurely. When behind-ear portion 206A is charged, portable case 204 may activate circuitry to switch the electro-permanent magnet of retention structure 212A to reduce the magnetic attraction between the two parts and enable mechanical disengagement of the charged behind-ear portion 206A with minimal force. Similar electro-permanent magnets may be used in tether 210 for varying the magnetic attraction between attachment feature 250 and behind-ear portion 206A depending on whether the parts are being mated together or separated.

Figure 3:
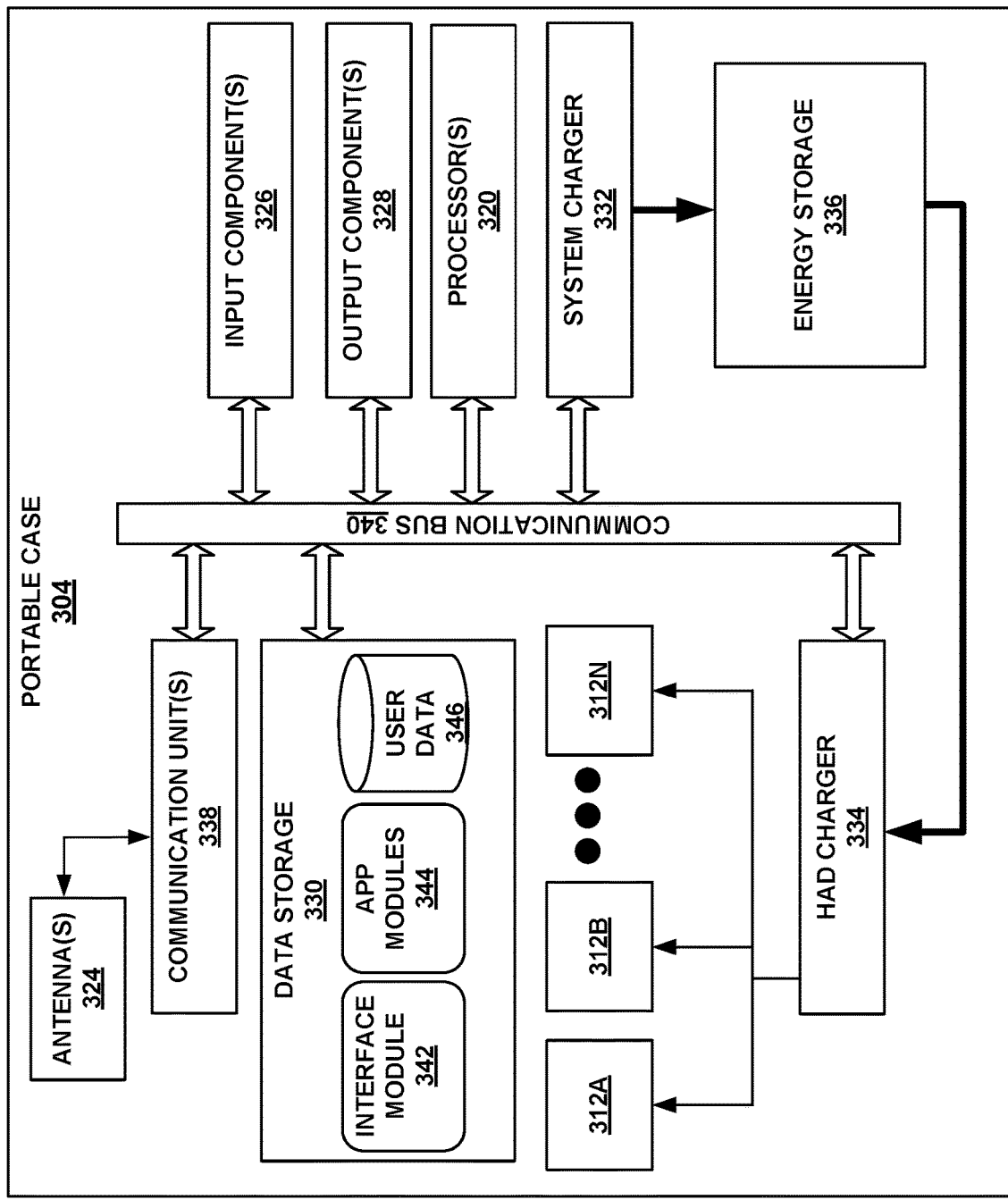
FIG. 3 is a block diagram illustrating an example portable case for storing and charging behind-ear portions of an example hearing assistance device, in accordance with one or more aspects of the present disclosure.

FIG. 3 is a block diagram illustrating an example portable case for storing and charging behind-ear portions of an example hearing assistance device, in accordance with one or more aspects of the present disclosure. Portable case 304 is an example of portable cases 104 and 204 of FIGS. 1, 2A, and 2B, and is described below in the context of FIGS. 1, 2A, and 2B. It should be understood that portable case 304 is only one example of a portable case according to the described techniques. Portable case 304 may include additional or fewer components than those shown in FIG. 3.

In the example of FIG. 3, portable case 304 includes one or more input components 326, one or more output components 328, one or more processors 320, data storage device 330, system charger 332, hearing assistance device (HAD) charger 334, one or more transceivers 322, one or more antennas 324, retention structures 312A-312N, energy storage device 336, one or more communication units 338, and communication bus 340. Data storage device 330 may include interface module 442, various application modules 444, and user data 446.

Communication bus 340 interconnects at least some of the components 322, 324, 326, 328, 320, 330, 332, 334, and 338 for inter-component communications. That is, each of components 322, 324, 326, 328, 320, 330, 332, 334, and 338 may be configured to communicate and exchange data via a connection to communication bus 340. In some examples, communication bus 340 is a wired or wireless bus. Communication bus may include a system bus, a network connection, an inter-process communication data structure, or any other method for communicating data.

Input components 326 are configured to receive various types of input, including tactile input, audible input, image or video input, sensory input, and other forms of input. Non-limiting examples of input components 326 include a presence-sensitive input device or touch screen, a button, a switch, a key, a microphone, a camera, or any other type of device for detecting input from a human or machine. Other non-limiting examples of input components 326 include one or more sensor components, such as a proximity sensor, a global positioning system (GPS) receiver or other type of location sensor, an accelerometer, an inertial measurement unit (IMU), a temperature sensor, a barometer, a gyro, an ambient light sensor, a proximity sensor, a hydrometer sensor, a heart rate sensor, a magnetometer, a glucose sensor, an olfactory sensor, a compass, a magnetometer, an antennae for wireless communication and location sensing, a step counter, to name a few other non-limiting examples.

Output components 328 are configured to generate various types of output, including tactile output, audible output, visual output (e.g., graphical or video), and other forms of output. Non-limiting examples of output components 328 include a sound card, a video card, a speaker, a display, a projector, a vibration device, a light, a light emitting diode (LED), or any other type of device for generating output to a human or machine.

One or more communication units 338 enable portable case 304 to communicate with external devices (e.g., computing devices 101 and/or HAD 102) via one or more wired and/or wireless connections to network 105. Communication units 338 transmit and receive signals being transmitted across network 105 and convert the network signals into readable data used by any of components 322, 324, 326, 328, 320, 330, 332, 334, and 338. One or more antennas 324 are coupled to communication units 338 and are configured to generate and receive the signals that are broadcast through the air (e.g., via network 105).

Examples of communication units 338 include various types of receivers, transmitters, transceivers, Bluetooth radios, short wave radios, cellular data radios, wireless network radios, universal serial bus (USB) controllers, proprietary bus controllers, network interface cards, optical transceivers, radio frequency transceivers, or any other type of device that can send and/or receive information over a network. In cases where communication units 338 include a wireless transceiver, communication units 338 may be capable of operating in different radio frequency (RF) bands (e.g., to enable regulatory compliance with a geographic location at which portable case 304 is being used). For example, a wireless transceiver of communication units 338 may operate in the 900 MHz or 2.4 GHz RF bands. A wireless transceiver of communication units 338 may be a near-field magnetic induction (NFMI) transceiver, and RF transceiver, an Infrared transceiver, ultra-sonic transceiver, or other type of transceiver.

In some examples, communication units 338 are configured as wireless gateways that manage information exchanged between portable case 304, and hearing assistance device 102, computing devices 101, and other hearing assistance devices. As a gateway, communication units 338 may implement one or more standards-based network communication protocols, such as Bluetooth®, Wi-Fi®, GSM, LTE, WiMax®, 802.1X, Zigbee®, LoRa® and the like as well as non-standards-based wireless protocols (e.g., proprietary communication protocols). Communication units 338 may allow HAD 102 to communicate, using a preferred communication protocol implementing intra and inter body communication (e.g., an intra or inter body network protocol), and convert the body communications to a standards-based protocol for sharing the information with other computing devices, such as computing devices 101. Whether using a body network protocol, intra or inter body network protocol, body area network protocol, body sensor network protocol, medical body area network protocol, or some other intra or inter body network protocol, communication units 338 enable HAD 102 to communicate with other devices that are embedded inside the body, implanted in the body, surface-mounted on the body, or being carried near a person's body (e.g., while being worn, carried in or part of clothing, carried by hand, or carried in a bag or luggage). For example, HAD 102 may cause behind-ear portion 106A to communicate, using an intra or inter body network protocol, with in-ear portion 108, when HAD 102 is being worn on a user's ear (e.g., when behind-ear portion 106A is positioned behind the user's ear while in-ear portion 108 sits inside the user's ear.

Energy storage 336 represents a battery (e.g., a well battery), a capacitor, or other type of electrical energy storage device that is configured to power each of the components of portable case 304. Energy storage 336 is coupled to system charger 332 which is responsible for performing power management and charging of energy storage 336. System charger 332 may be a buck converter, boost converter, flyback converter, or any other type of AC/DC or DC/DC power conversion circuitry adapted to convert grid power to a form of electrical power suitable for charging energy storage 336. In some examples, system charger 332 includes a charging antenna (e.g., NFMI, RF, or other type of charging antenna) for wirelessly recharging energy storage 336. In some examples, system charger 332 includes photo-voltaic cells protruding through a housing of portable case 104 for recharging energy storage 336. System charger 332 may rely on a wired connection to a power source for charging energy storage 336.

Retention structures 312A-312N (collectively referred to as "retention structures 312") are examples of retention structures 112 and 212 of FIGS. 1 and 2. For example, retention structures 312 are configured to receive behind-ear portions 106 for charging. Retention structures 312 may discharge behind-ear portions 106 when charged. Retention structures 312 may include mechanical and/or magnetic attachment features that, after manipulation by a user, automatically attach or detach behind-ear portions 106. Each of retention structures 312 is electrically coupled to energy storage 336 and HAD charger 334. When HAD charger 334 enables retention structures 312 for charging, electrical current passes from energy storage 336 to retention structures 312 (e.g., via some charging circuitry).

Retention structures 312 may provide a magnetically coupled electrical connection between a power source of a behind-ear portion 106 and HAD charger 334. Retention structures 312 may include one or more mechanical stops to ensure correct seating of behind-ear portions 106 and/or to prevent removal of behind-ear portions 106 when charging. Retention structures 312 may include respective retention structures that enable easy insertion of depleted behind-ear portions 106 and locks the depleted behind-ear portions 106 in place. The mechanical and/or magnetic attachment features of retention structures 312 may enable easy insertion of behind-ear portions 106 and may require a sufficient amount of force to overcome the mechanical and/or magnetic attachment features during removal.

In some examples, retention structures 312 include a magnetic or spring-loaded latch. For example, retention structures 312 may each be an approximate cylindrical shaft, with partial grooves down the length of each shaft. When behind-ear portions 106 are pushed inside retention structures 312, they are retained by two opposing spring loaded or magnetic catches inside retention structures 312. The partial grooves prevent the spring loaded or magnetic catches from being released. Since the grooves in each shaft do not extend all the way around the diameter of the shaft, in this example, behind-ear portions 106 may be rotated (e.g., ninety-degrees) to a point where there are no grooves in the shaft that are in contact with the catches of behind-ear portions 106. With no grooves to retain behind-ear portions 106 in each shaft, the behind-ear portions 106, after rotation, can be removed from retention structures 312.

In some examples, retention structures 312 include a mechanical feature or mechanical catch that may prevent two parts from being detached without sufficient force for overcoming the mechanical catch. And, in the case of a magnetic feature, the attachment features may be a mechanically and/or magnetically self-aligning design. That is, to configure behind-ear portion 106 for use, a user may simply bring an attachment feature of retention structures 312 near an attachment area of behind-ear portion 106 and the magnetic attraction between the attachment feature and the attachment area of behind-ear portion 106 may force the two parts together and enable an electrical connection between the two parts. Similarly, to configure behind-ear portion 106 for storage or charging in portable case 104, a user may simply position the attachment area of behind-ear portion 106 above an empty one of retention structures 312, and the magnetic attraction between the empty retention structure 312 and the attachment area of behind-ear portion 106 may allow a user to simply drop behind-ear portion 106 into the empty retention structure 312 where the electrical contacts of behind-ear portion 106 may automatically align with the charging contacts of the empty one of retention structures 312.

HAD charger 334 includes charging circuitry that is electrically coupled to each of retention structures 312 and is responsible for enabling or disabling each of retention structures 312 for charging power sources in behind-ear portions 106. HAD charger 334 may further exchange data between behind-ear portions 106 located in retention structures 312 and other components of portable case 304. HAD charger 334 may cause the magnetic connection between the power source of a behind-ear portion 106 and HAD charger 334 to be stronger when charging the power source and weaker or reversed after the power source is charged (e.g., using electro-permanent magnets activated and deactivated by circuitry). Such electro-permanent magnets may be configured by a pulse of energy supplied by energy storage 336 and HAD 334. Such energy may be supplied from HAD 334 through direct connection or magnetic induction to the electro-permanent magnet. It should be understood that one or more electro-permanent magnets may be included in either, or both, a behind-ear portion of an example hearing assistance device and portable case 304. Furthermore, any combination of any of the following: electro-permanent magnets(s), permanent magnet(s), and ferrous material, may be used by at least one of a behind-ear portion of an example hearing assistance device and portable case 304 to achieve a strong bond between portable case 304 and the charging behind-ear portion.

HAD charger 334, in some examples, can detect the positive and negative contacts in a behind-ear portion of a HAD that is seated in one of retention structures 312 and adjust its internal circuitry to correctly charge the behind-ear portion power source. Automatic alignment detection by HAD charger 334 may improve usability; a user may not be required to correctly align and insert behind-ear portions 106 into portable case 304 since HAD charger 334 automatically configures portable case 304 to accept behind-ear portions 106 regardless as to how behind-ear portions 106 are inserted into retention structures 312. In other embodiments the correct polarity is ensured by magnetic alignment or by mechanical alignment.

One or more processors 320 execute operations that implement functionality of portable case 304. One or more processors 320 may be implemented as fixed-function processing circuits, programmable processing circuits, or a combination of fixed-function and programmable processing circuits. Examples of processors 320 include digital signal processors, general purpose processors, application processors, embedded processors, graphic processing units (GPUs), digital signal processors (DSPs), application specific integrated circuits (ASICs), field programmable gate arrays (FPGAs), display controllers, auxiliary processors, sensor hubs, input controllers, output controllers, microcontrollers, and any other equivalent integrated or discrete hardware or circuitry configure to function as a processor, a processing unit, or a processing device.

Data storage device 330 of portable case 304 represents one or more fixed and/or removable data storage units configured to store information for subsequent processing by processors 320 during operations of portable case 304. In other words, data storage device 330 retains data accessed by modules 342 and 344 as well as other components of portable case 304 during operation. Data storage device 330 may, in some examples, includes a non-transitory computer-readable storage medium that stores instructions, program information, or other data associated modules 342 and 344. Processors 320 may retrieve the instructions stored by data storage device 330 and execute the instructions to perform operations described herein.

Data storage device 330 may include a combination of one or more types of volatile or non-volatile memories. In some cases, data storage device 330 includes a temporary or volatile memory (e.g., random access memories (RAM), dynamic random-access memories (DRAM), static random-access memories (SRAM), and other forms of volatile memories known in the art). In such a case, data storage device 330 is not used for long-term data storage and as such, any data stored by storage device 330 is not retained when power to data storage device 330 is lost. Data storage device 330 in some cases is configured for long-term storage of information and includes non-volatile memory space that retains information even after data storage device 330 loses power. Examples of non-volatile memories include magnetic hard discs, optical discs, flash memories, USB disks, or forms of electrically programmable memories (EPROM) or electrically erasable and programmable (EEPROM) memories.

Modules 342 and 344 represent any combination of hardware, software, and firmware units that are operable by processors 320 to perform operations of portable case 304. For example, processors 320 may retrieve and execute instructions stored by data storage device 330 that cause processors 320 to perform the operations of modules 342 and 344. By executing the instructions associated with modules 342 and 344, processors 320 may store or write information to data storage device 330.

Interface module 342 implements a user interface associated with portable case 304, for example, by translating inputs detected by portable case 304 to commands for performing operations or generating corresponding outputs. Interface module 342 receives information about inputs detected by input components 326 and in response, generates information for causing output components 328 to produce output. For example, interface module 342 may receive information from a microphone of input components 326, determine that a user is speaking a command to portable case 304, and perform an operation in response.

Interface module 342 may detect two-dimensional and/or three-dimensional gestures as input from a user of portable case 304. For instance, a sensor or IMU of input components 326 may detect a user's movement (e.g., moving a hand, an arm, a pen, a stylus, etc.) within a threshold distance of the sensor. Interface module 342 may determine a two or three-dimensional vector representation of the movement and correlate the vector representation to a gesture input (e.g., a hand-wave, a pinch, a clap, a pen stroke, etc.) that has multiple dimensions. Interface module 342 may receive information from an IMU of input components 326, determine that a user is performing a hand gesture with portable case 304 in-hand, and perform an operation in response.

Interface module 342 may provide a graphical user interface, an audible user interface, a haptic interface, or a combination thereof. The user interface provided by interface module 342 may in some examples a battery gauge. The battery gauge may indicate battery levels of behind-ear portions 106 that are seated in retention structures 312. The battery gauge may indicate a battery levels of energy source 336. A user may interact with the battery gauge provided by interface module by providing verbal inputs (e.g., to a microphone of input components 326), touch inputs (e.g., to a touch screen of input components 326), or via haptic components (e.g., detected by an IMU of input components 326). For example, if a user shakes portable case 304, the movement detected by movement sensors of input components 326 may indicate to interface module 342 that a user wishes to learn the charging status of behind-ear portions 106. In response to the shake input, interface module 342 may cause a speaker of output components 328 to generate audible output that "speaks" the battery level to the user. Other combinations of touch, voice, or haptic input and visual, audible, and haptic outputs are possible.

Application modules 344 include any application or software that portable case 304 may execute to implement the functionality of portable case 304 that is described in this disclosure. For example, application modules 344 may include machine-learning or artificial intelligence software (e.g., for configuring portable case 304 or any HAD operatively and communicatively coupled to portable case 304, such as HAD 102), an Internet browser, a media player, a file system, a map or navigation program, or any other number of applications or features that portable case 304 may include. Other examples of application modules 344 include programming software for using portable case 304 as a programmer for HAD 102, a personal assistant application, a messaging or personal communication application, an audio recording application, or other application.

In some cases, application modules 344 include an audio controller application. The audio controller application may interact with communication units 338 to scan for available wireless audio broadcasts within range of antennas 324 and cause interface module 342 to alert a user of potential audio sources (e.g., via audible, tactile, or visual feedback). The audio controller application may receive information obtained by interface module 342 (e.g., after input components 326 detect spoken or touch inputs from a user) that is interpreted by the audio controller application as an input to select a particular audio source or broadcast.

Application modules 344, in some examples, include a remote-control application. The remote-control application enables a user to provide inputs to portable case 304 that alter settings of a hearing assistance device, such as HAD 102, or some other computing device, such as one of computing devices 101.

Application modules 344 may include a remote microphone application. The remote microphone application enables a user to position portable case 304 near a desired audio source (e.g., another person, a speaker, etc.) and hear the audio being picked up by portable case 304, in his or her ear as the audio is played back via HAD 102. For instance, the remote microphone application may cause a microphone of input components 326 to start recording audio. In seemingly near real-time, the remote microphone application processes the recorded audio and sends the recorded audio via communication units 328 to HAD 102, or some other external device.

Application modules 344 may include a personal assistant application or other artificial intelligence application that interacts with a user to perform various functions. For example, the assistant may help a user configure a hearing instrument for a particular environment, access the Internet to perform various tasks on behalf of the user, or perform other assistant functionality.

Artificial intelligence capability provided by application modules 344 could be distributed (with varying degrees of capability) amongst various components connected to network 105. For example, the artificial intelligence capability may execute in whole or part at portable case 304, HAD 102, other personal electronics in a body-area-network, and at computing devices 101 (e.g., in a cloud-based networked application environment).

With permission from a user, an artificial intelligence application may monitor conversations being detected by a microphone of input components 326 using voice recognition techniques (e.g., identifying a quantity of individual participants and their roles in the conversation), and when necessary perform targeted cloud-based searches on behalf of the user or near real-time translations. The artificial intelligence application may cause portable case to audibly, visually, or using haptic feedback, coach the user by causing output components 328 to output additional data, answers to questions, or cues when needed.

In some cases, the artificial intelligence application could be used to interpret speech in the context of a conversation and "regenerate" a much higher signal-to-noise ratio version of the received audio by performing word or speech synthesis. The artificial intelligence application may cause portable case 304 to output (e.g., in a computer-generated voice synthesized by the artificial intelligence application that in some cases mimics the original source) the regenerated audio either via a speaker embedded in output components 328, or via a speaker embedded in in-ear portion 108 of HAD 102. The regenerated audio may in some cases be translated from one language to another, in some instances, even correcting for grammatical errors. Such a feature may significantly reduce or off-load the cognitive burden a user may otherwise experience listening to speech in a noisy environment. In other applications, the neural network may be employed to make automatic adjustments to HAD 102 based on the acoustic environment that the wearer is in. These adjustments may be based on sound the microphone picks up from either portable case 304 or HAD 102, themselves. Other adjustments may be more direct from voice commands from the user.

In some examples, the artificial intelligence application comprises a neural network. For example, the artificial intelligence application may include a neural network for sound processing, sound classification, and object or image classification. In such an example, portable case 304 may include (or be communicatively coupled to one located in HAD 102) an ultrasonic transducer and sensor for determining range to objects and density of objects. As such, portable case 304 may execute the artificial application to perform (e.g., body-word) assistance and navigation for a seeing impaired user.

User data 346 includes any information stored by portable case 304 on behalf of a user. User data 346 includes preferences or settings associated with portable case 304 and HAD 102. User data 346 may include calendar information, messages, alerts, warnings, alarms, e-mails, address book or contact information, music files, audio book files, or other audio files that a user of portable case 304 may wish to access, e.g., via a media player application 344 executing at portable case 304. User data 346 may be stored on removable media of data storage 330. A user may swap out the removable storage media for removable storage media that includes other music, audio books, etc. In some cases, user data 346 includes medical or financial records of the user, and other information that the user may want to have on hand at all times. For example, user data 346 may include an audio recording of a user's medical insurance record, medical records, and medical alerts. User data 346 may include a digital wallet with personal credit card or cryptocurrency information.

Application modules 344 may utilize user data 346 to perform an operation. Application modules 244 may write or modify user data 346. For example, an assistant application may utilize user data 346 to complete a task (e.g., when a user commands the assistant to tell the user about his or her daily schedule).

Portable case 304 and data storage 330 may ensure that user data 346 is encrypted, secure, and/or password protected to prevent malicious use. Such passwords or encryption keys may be authenticated via sensory information obtained from HAD 102 or other external device. For example, a user may speak a password, the spoken audio may be picked up by a microphone of input components 326 or a microphone of HAD 102. Using voice-recognition, face-recognition, or authentication techniques, portable case 304 may validate the user (e.g., the user's voice, fingerprint, or facial image) or invalidate the user. In response to validating the password or key, portable case 304 may unlock and grant access to user data 346. In response to invalidating the voice input, portable case 304 may prevent access to user data 346. In other examples, passwords and keys could be authenticated via on-board biometry sensors of input components 326 (e.g., a fingerprint sensor, a temperature sensor, a camera or image sensor configured to perform facial recognition, or other sensor) or HAD 102. In some examples, in response to HAD 102 or portable case 104 authenticating a user (e.g., a wearer of HAD 102), HAD 102 and/or portable case 104 may act as a "universal password wallet/or key repository" that communicates via an encrypted/secure wireless connection with other wirelessly enabled devices that require user authentication before granting access to the other wirelessly enabled devices (e.g. computers, smart-phones, automobile automation/locks, home automation/locks, etc.)

Figure 4:
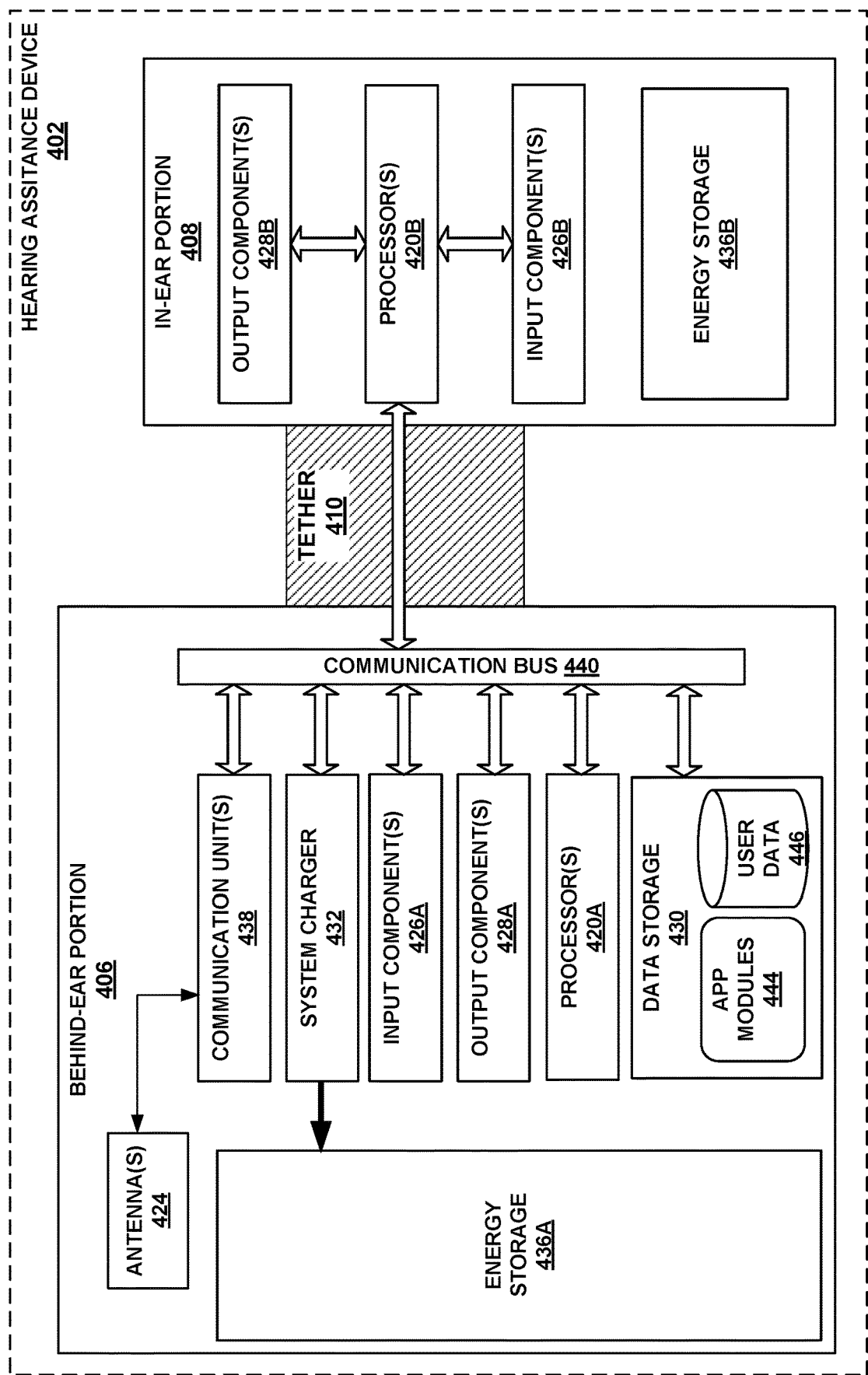
FIG. 4 is a block diagram illustrating an example hearing assistance device, in accordance with one or more aspects of the present disclosure.

FIG. 4 is a block diagram illustrating an example hearing assistance device 402, in accordance with one or more aspects of the present disclosure. As shown in the example of FIG. 4, hearing assistance device (HAD) 402 includes behind-ear portion 406 operatively coupled to in-ear portion 408 via tether 410. HAD 402 is an example of HAD 102, 202, 202A and 202B of FIGS. 1 and 2A-2D. HAD 402 is described in the context of FIGS. 1 and 2A-2D. It should be understood that HAD 402 is only one example of a hearing assistance device according to the described techniques. HAD 402 may include additional or fewer components than those shown in FIG. 4.

Examples of each of the components of HAD 402 include the examples of each of the similarly-named components of portable case 304 described above. For instance, processors 420A and 420B may be similar to examples of processors 320 described above and examples of input components 426A and 426B and output components 428A and 428B include the respective examples of input components 326 and output components 328 described above. In addition, processors 420A and 420B may include or access local memory of behind-ear portion 406 and in-ear portion 408, respectively, to perform the operations described herein.

Tether 410 operatively (e.g., electrically, physically, and communicatively) couples behind-ear portion 406 with in-ear portion 408. Tether 410 is an example of tethers 110 and 210 and uses a combination of one or more wired communication links to transfer information and electrical energy between portions 406 and 408. Tether 410 may be configured as a handle for a user to grip HAD 402.

In-ear portion 408 is a part of HAD 402 responsible for outputting sound for hearing. In-ear portion 408 includes core electro-acoustic features of HAD 402, including one or more processors 420B, such as one or more digital signal processors, one or more output components 428B, such as a speaker, and one or more input components 426B, such as a microphone. In-ear portion 408 may include additional components (e.g., acoustic filters and other components) that are not shown in FIG. 4.

One or more processors 420B may exchange information via tether 410 with behind-ear portion 406. One or more processors 420B may receive information from behind-ear portion 406 via tether 410 and perform an operation in response. Likewise, one or more processors 420B may transmit information to behind-ear portion 406 via tether 410 to cause behind-ear portion 406 to perform an operation in response.

For example, processors 420B may receive an indication of an audio data stream being output from behind-ear portion 406 and in response, cause output components 428B to produce audible sound representative of the audio stream. In another example, a biometric sensor of input components 426B may detect a physiological condition (e.g., heart rate, body temperature, blood sugar level, or other physiological condition) or a movement sensor of input components 426B may detect a change in movement (e.g., a change in biometric pressure, an acceleration, or other change in movement). Processors 420B may send an indication of the physiological condition or change in movement via tether 410 to behind-ear portion 406 for further processing, such as for executing a fall-detection algorithm, determining a user's health, detecting a three-dimensional gesture (e.g., a head shake or head nod), or performing some other operation based on data received from in-ear portion 408.

In this way, HAD 402 can rely on additional processing power provided by behind-ear portion 406 to perform more sophisticated operations and provide more advanced features than other hearing instruments. In some examples, HAD 402 sends information via behind-ear portion 406 to a portable case, such as portable cases 104, 204, and 304, for further offline processing, thus (indirectly) expanding even further the processing capabilities of in-ear portion 408. And as described above, portable cases 103, 204, 304, may provide additional offline processing on behalf of behind-ear portion 406 by utilizing a cloud-based service or relying on assistance from one of computing devices 101 that is coupled to network 105.

In addition to the components described above, HAD 402 includes energy storage 436B for enabling in-ear portion 408 to operate as a stand-alone hearing instrument without being operatively coupled to tether 410 and behind-ear portion 406. For example, a user may prefer to normally wear tether 410 and portions 406 and 408 during everyday use. However, when a user prefers to go without behind-ear portion 406 and tether 410 (e.g., for aesthetic reasons, when exercising, when working, or at any other time a user chooses to only wear in-ear portion 408), energy storage 436B provides sufficient electrical energy storage to power in-ear portion 408 during such times. Energy storage 436B may not be intended to provide sufficient electrical energy for all-day use of in-ear portion 408; rather energy storage 436B may provide one or more hours of use without altering the form-factor of in-ear portion 408 that enables in-ear portion 408 to be concealed in a user's ear canal.

Behind-ear portion 406 is a part of HAD 402 responsible for supporting in-ear portion 408 in outputting sound for hearing. In some examples, behind-ear portion 406 includes some or all of the components of in-ear portion 408 shown in FIG. 4. Behind-ear portion 406 may include some of the components and perform some of the functionality attributed to in-ear portion 408 in the above description, for example, to reduce a physical size of in-ear portion 408 or otherwise reduce complexity of in-ear portion 408. For example, in-ear portion 408 may support autonomous functionality (e.g., by operating independent of behind-ear portion 406 and tether 410). In such an example, in-ear portion 408 includes tether connections and some or all of the components shown in FIG. 4 including an energy source as shown in FIG. 4. In some examples, in-ear portion 408 includes additional memory for storing user data.

In the example of FIG. 4, behind-ear portion 406 includes one or more processors 420A, system charger 432, one or more output components 428A, one or more input components 426A, energy storage 436A. Behind-ear portion 406 further includes, in this example, one or more antennas 424, one or more communication units 438, data storage device 430, and communication bus 440. Within data storage device 430 are one or more application modules 444 and user data store 446.

Behind-ear portion 406 may be primarily configured as a detachable, modular component that houses a rechargeable energy source. For example, system charger 432 may include an electromagnetic transducer that is completely or partially contained within, or on, a housing of behind-ear portion 406 for receiving electrical energy for purposes of charging energy source 436A. System charger 432 may include an inductive charging coil, or antenna with a pulse width modulation integrated circuit (PWMIC) and/or rectifier. System charger 432 may be configured to receive electrical energy when behind-ear portion 406 mates with a charging retention structure of portable cases 104, 204, and 304 and store the received electrical energy in energy storage 436A.

In addition to providing electrical energy, the components of behind-ear portion 406 may further configure portion 406 to perform various other advanced functions. These other advanced functions include advanced battery functions such as, but not limited to: short-circuit protection, polarity detection, charging status or alerts, storage reserve capacity, graceful power shutdown, emergency power conservation mode, fast-charging options, and other advanced battery functions. For example, one of application modules 444, executing at processors 420A, may receive information from system charger 432 or directly from energy storage 436A and cause processors 420A to present, based on the received information, battery health and status information via a user interface provided by behind-ear portion 406, and/or the user interface provided by portable cases 104, 204, and 306.

The user interface provided by behind-ear portion 406 may present an audible or haptic type user interface to the user relying on output components 428A and/or output components 428B of in-ear portion 408. For instance, processors 420A may send data to processors 420B that cause processors 420B to use output components 428B to generate sounds, audible cues, haptic feedback, or other alerts to information such as, battery health, battery life, time remaining, storage reserve or capacity, or other information. In reverse, a user interface provided by behind-ear portion 406 may receive commands from the user by relying on input components 426A and/or input components 426B of in-ear portion 408. For instance, processors 420A may receive data from processors 420B indicative of sounds, audible cues, or other information received by input components 426B as a user interacts with the user interface. Processors 420A may perform operations or alter the user interface based on the data received from processors 420B.

Other advanced functions that may be provided by behind-ear portion 406, in various examples, include communication functions enabled by communication units 438 and antennas 424. Behind-ear portion 406 may enable in-ear portion 408 to communicate with external devices, such as computing devices 101, in addition to enabling communication with other hearing instruments. For example, one of application modules 444 (e.g., a media playback application) executing at processors 420A may receive an encoded audio stream from one of computing devices 101, convert the encoded audio stream to a different format that is suitable for consumption by in-ear portion 408, and cause processors 420A to send the converted audio stream to processors 420B of in-ear portion 408 for subsequent decoding and playback to a user. Alternatively, one of application modules 444 may receive an encoded audio stream from in-ear portion 408, convert the encoded audio stream to a different format that is suitable for consumption by computing devices 101, and cause processors 420A to send the converted audio stream, via communication units 438, to computing devices 101 or portable cases 104, 204, or 304. In this way, in-ear portion 408 and behind-ear portion 406 can communicate together and with other hearing instruments using more reliable intra or inter body network protocols while simultaneously supporting communication outside the body using cellular, LTE, Bluetooth®, Wi-FI®, and other communication protocols that are supported by external devices, such as computing devices 101.

Other advanced functionality provided by behind-ear portion 406 include operating in a second mode when not being worn by a user (e.g., not tethered to in-ear portion 408) that is different than the mode behind-ear portion 406 operates-in when being word by the user. For example, processors 420A may detect when behind-ear portion 406 is detached from tether 410. In response to detecting that tether 410 is not operatively coupled to behind-ear portion 406, one of application modules 444 may cause processors 420A to perform autonomous functions, such as operating as a miniature multi-functional hearing assistance device accessory. In such a mode, behind-ear portion 406 may configure input components 426A to act as a wireless, remote microphone, or may configure communication units 438 to extend the range of communication signals being transmitted or received by portable cases 104, 204, and 304, in-ear portion 408, or one of external computing devices 101. In some examples, even though tether 410 may be removed from behind-ear portion 406, behind-ear portion 406 may still maintain a wireless communication connection with in-ear portion 408. Specifically, while operating in the second mode, a communication unit and/or antenna of in-ear portion 408 (not shown in FIG. 4) may wirelessly exchange communication signals with antennas 424 and communication units 438 of behind-ear portion 406, e.g., to transmit data representative of audio received by a microphone associated with behind-ear portion 406 to in-ear portion 408. As an illustration, the user may remove the behind-ear portion 406 and place it proximate to another person to capture speech emitted by the person for transmission to the in-ear portion 408, facilitating better conversational hearing, e.g., in a noisy environment.

As another example, when operating in the second mode when not being worn, behind-ear portion 406 may configure processors 420A to operate as a wireless audio controller that enables indirect, wireless pairing of in-ear portion 408 to portable cases 104, 204, and 304, in-ear portion 408, or one of external computing devices 101. By relying on behind-ear portion 406 for audio controller functions, in-ear portion 408 may offload connection management processing that in-ear portion 408 might otherwise be required to perform to communicate wirelessly with other devices, and as such, may reduce the rate of power consumption by in-ear portion 408 and thereby extend the energy reserve of energy storage 436B.

In any case, behind-ear portion 406 may perform the operations described herein while behind-ear portion 406 charges energy storage 436A from inside portable cases 104, 204, and 304. Likewise, behind-ear portion 406 may perform the operations described herein while behind-ear portion 406 is no longer charging and/or is located outside portable cases 104, 204, and 304.

Figure 5:
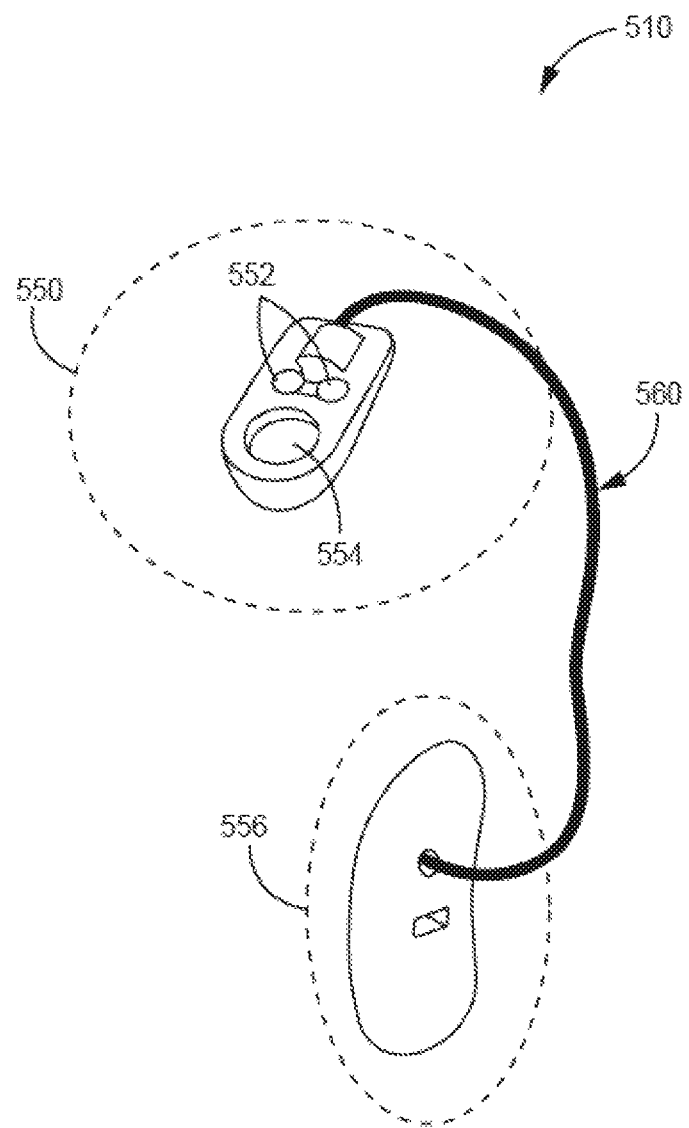
FIG. 5 is a conceptual diagram illustrating an example tether for coupling a behind-ear portion of an example hearing assistance device to an in-ear portion of the example hearing assistance device, in accordance with one or more aspects of the present disclosure.

FIG. 5 is a conceptual diagram illustrating an example tether for coupling a behind-ear portion of an example hearing assistance device to an in-ear portion of the example hearing assistance device, in accordance with one or more aspects of the present disclosure. Tether 510 is an example of tethers 110, 210, and 410 of FIGS. 1, 2A through 2D, and 4 and is described in the context of the preceding FIGS. Tether 510 includes behind-ear attachment 550, in-ear attachment 556, and coupling apparatus 560.

In the example of FIG. 5, coupling apparatus 560 is configured to transmit one or more electrical signals, for communication and/or energy transfer, between behind-ear attachment 550 and in-ear attachment 556. For example, coupling apparatus 560 may include one or more elongated, electrical conductors (e.g., copper wires), one or more fiber optic links, or one or more infrared links, or one or more other links made from any other suitable type of electrical transmission media, any of which may be carried in or covered by an insulative cover or coating.

Attachments 550 and 556 use one or more attachment features to operatively couple tether 510 to in-ear and behind-ear portions of an example hearing instrument. Such attachment features may be magnetic, electro-mechanical, mechanical, or some combination thereof. In a simple case, attachments 550 and 556 provide two or more respective contacts that when mated with respective electrical conductors on the in-ear and behind-ear portions, conduct electrical energy being transferred from internal energy storage components of the in-ear and behind-ear portions.

In the example of FIG. 5, attachment 550 includes contacts 552 and 554. Although not shown in FIG. 5, attachment 556 may include similar contacts. Attachment 556 may in some cases be permanently attached to, and form part of, an in-ear portion of an example hearing instrument, such as in-ear portion 408 of HAD 402. In other cases, attachment 556 is similar to attachment 550 in that both attachments 550 and 556 are detachable from behind-ear portions and in-ear portions an example hearing instrument, such as in-ear portion 408 of HAD 402.

Contacts 552 are configured to mate with corresponding electrical contacts on a behind-ear portion of an example hearing instrument. Contact 554 may be configured to mate with a corresponding magnetic contact on a behind-ear portion of an example hearing instrument. In some examples, contacts 552 and 554 represent magnetic fixation elements, electrical connections, mechanical connections, or some combination of magnetic, electrical, and physical connections.

Contacts 552 and 554 may be co-axial with the corresponding contacts on the behind-ear portion, thereby preventing a user from incorrectly attaching tether 510 to the behind-ear or in-ear portions of an example hearing instrument. Contacts 552 and 554 may provide both mechanical or electrical connections as well as physical fixation to corresponding contacts on a behind-ear portion.

In some examples, contacts 552 and 554 are coated to improve electrical conduction and magnetic fixation. For instance, contacts 552 and 554 may be gold-plated so that multiple instances of magnetic "fixation" are provided between tether 510 and behind-ear and in-ear portions of an example hearing instrument. Furthermore, the gold-plating may enable multiple very low electrical resistance connections as well. In some examples, contacts 552 and 554 are formed from non-oxidizing, low-resistance material (e.g., copper-nickel-gold metal, stainless steel, German silver or copper-zinc-gold, palladium alloys, as well as other suitable materials) that provides mechanical fixation as well electrical conduction.

Figure 6A:
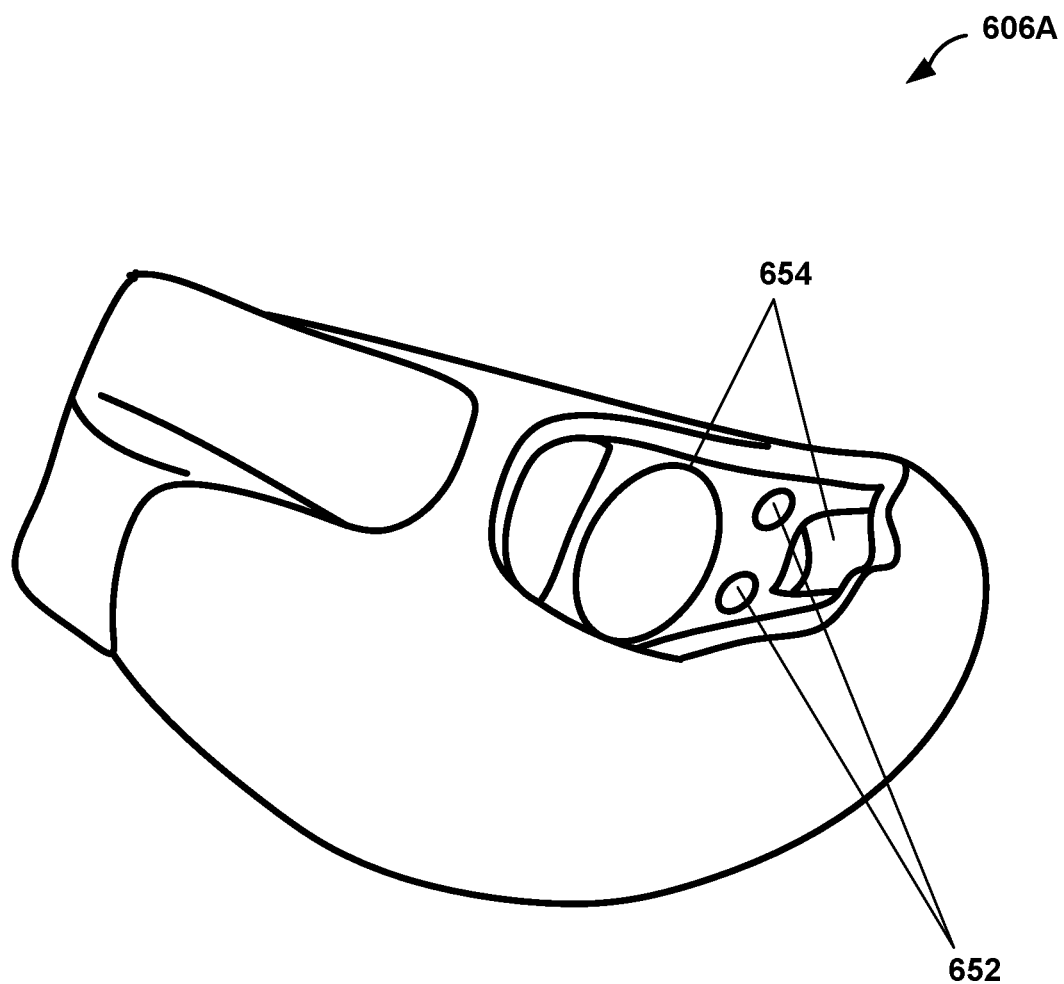
FIGS. 6A through 6C are conceptual diagrams illustrating example behind-ear portions of an example hearing assistance device, in accordance with one or more aspects of the present disclosure.
Figure 6B:
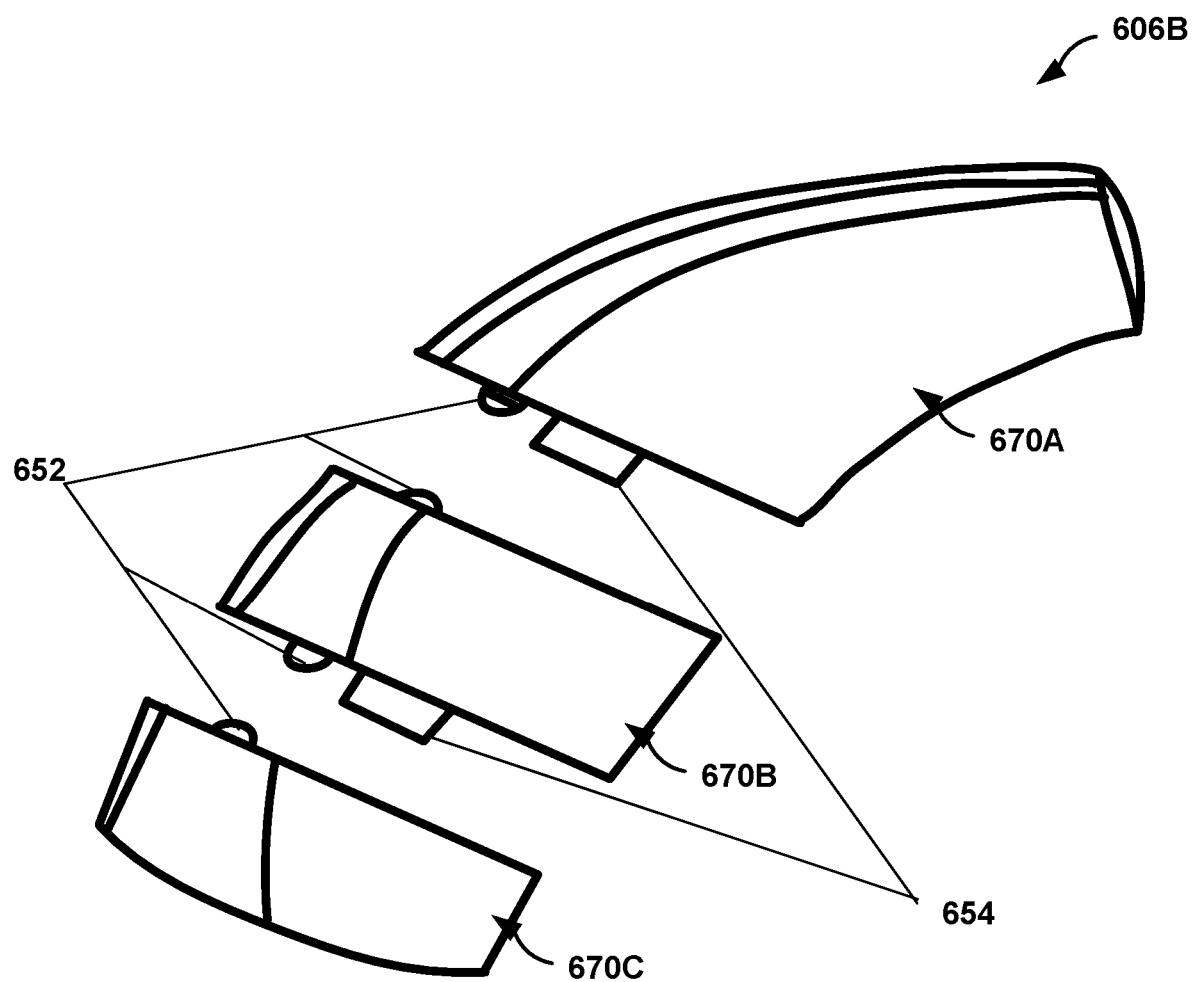
Figure 6C:
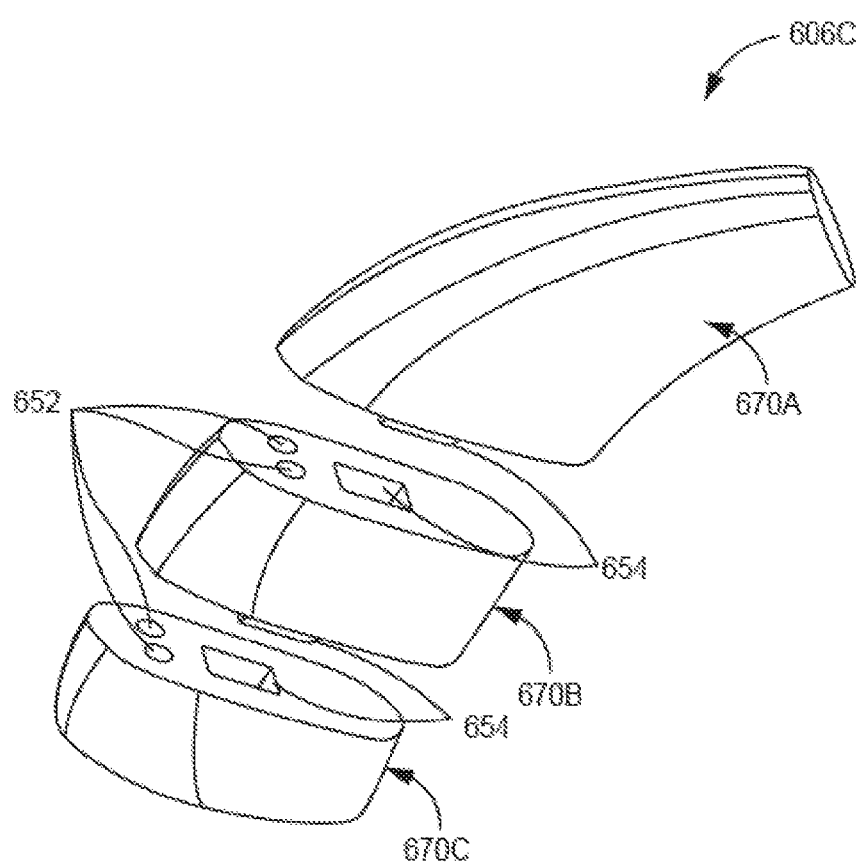

FIGS. 6A through 6C are conceptual diagrams illustrating example behind-ear portions of an example hearing assistance device, in accordance with one or more aspects of the present disclosure. Behind-ear portions 606A, 606B, and 606C of FIGS. 6A through 6C are examples of behind-ear portions 106, 206, and 406 of FIGS. 1, 2A through 2D, and 4 and are described in the context of the preceding figures.

In the example of FIG. 6A, behind-ear portions 606A includes contacts 652 and 654. Contacts 652 and 654 are similar, and reciprocal to contacts 552 and 554 of tether 510 of FIG. 5. For example, contacts 652 is designed to mate with contacts 552 of tether 510 and contact 654 is configured to mate with contacts of tether 510. Contacts 652 and 654 represent magnetic fixation elements, electrical connections, mechanical connections, or some combination of magnetic, electrical, and physical connections. Contacts 652 and 654 may include electro-permanent magnet connections.

To improve usability, behind-ear portion 606A may be symmetric; in other words, behind-ear portion 606A may rely on a housing that enables its installation in a portable case or to a tether with multiple orientations. Therefore, a user need not worry about installing behind-ear portion 606A incorrectly in a charging case or to a tether.

Contacts 652 and 654 may be co-axial or otherwise keyed with the corresponding contacts on the tether; thereby preventing a user from incorrectly attaching the tether to behind-ear portion 606A. Contacts 652 and 654 may provide both mechanical or electrical connections as well as physical fixation to corresponding contacts on an example tether.

In some examples, contacts 652 and/or 654 are coated to improve electrical conduction and magnetic fixation. For instance, contacts 652 and 654 may be gold-plated so that multiple instances of magnetic "fixation" are provided between a tether and behind-ear portion 606A. In some examples, contacts 652 and 654 are formed from non-oxidizing, low-resistance material (e.g., copper-nickel-gold metal, stainless steel, German silver or copper-zinc-gold, palladium alloys, as well as other suitable materials) that provides mechanical fixation as well electrical conduction.

Behind-ear portions 606B and 606C are example behind-ear portions formed of multiple sub-portions (also sometimes referred to herein as "chicklets") 670A, 670B, and 670C (collectively "sub-portions 670). Although each of behind-ear portions 606B and 606C is shown as having three separate sub-portions 670, in other examples, behind-ear portions 606B and 606C have two separate sub-portions 670 or more than three separate sub-portions 670.

Each sub-portion 670 mates with another sub-portion 670 via contacts 652 and 654. Each sub-portion 670 may provide a specific functionality. Each of sub-portions 670 may be swappable for a different sub-portion. The individual components of behind-ear portion 408 shown in FIG. 4 may be distributed amongst different sub-portions 670. By mixing and matching various types of sub-portions 670, a user can customize each of behind-ear portions 606B and 606C for a particular situation. For example, sub-portion 670A may be designated as a rechargeable power supply that provides operating power to behind-ear portion, sub-portion 670B may be a radio module that provides wireless telecommunication between the behind-ear portion and another device (such as charging case 304), and sub-portion 670C may be a sensor module that senses, e.g., one or more physiological conditions or signals.

In general, any component of portable case 304 of FIG. 3 and modules 406 and 408 of FIG. 4 may be included in one or more sub-portions 670. Examples of sub-portions 670 include various power sources, radio modules, sensor modules, output components, input components, and other types of components.

Sub-portion 670B may be a Bluetooth® radio and a user may wish to exchange sub-portion 670B for a different radio module, such as a Wi-Fi® or cellular radio to configure behind-ear portions 606B and 606C for communicating on a Wi-Fi® or cellular network as opposed to a Bluetooth® network. Sub-portion 670C may be a programming module that a physician or other user attaches to behind-ear portion 606B, for instance, to re-program an in-ear portion, such as in-ear portion 408 of FIG. 4. In some examples, sub-portion 670B and any other one of sub-portions 670 may be configured as a software-defined radio for performing multi-mode communications with a single "radio" hardware component. And in some examples, sub-portion 670B and any other one of sub-portions 670 may be configured as a near field magnetic induction radio (NFMI).

When configured as a sensor module, sub-portion 670A may include one or more biological and/or physical sensor types. Some non-limiting examples of sensor types include temperature, photovoltaic, pressure, electroencephalography, heart-rate, respiration rate, oxygen level, blood-glucose, intra-ocular, electrocardiogram, movement, or any other sensor type. When configured as sensors, sub-portions 670 may cooperatively communicate, e.g., via a wireless body area network (WBAN), with other sub-portions 670 and other intra or inter body wireless sensors that are unrelated to the hearing instrument.

A user may combine various types of sub-portions 670 to form a first behind-ear portion 606B or 606C for his or her left ear and may combine different types of sub-portions 670 to form a second behind-ear portion 606B or 606C for his or her right ear. In some examples, sub-portions 670 can be attached in any order to form a behind-ear portion 606. Accordingly, sub-portions 670 enable asymmetrically distributed functionality amongst binaural hearing assistance device. That is, rather than utilize two similar hearing instruments, with one in each ear, a user may benefit from having two different hearing instruments, one in each ear, that are operatively coupled to form a single, binaural hearing assistance system. Such a hearing assistance system may offer more capability and functionality than a traditional binaural hearing assistance system that relies on a similar hearing instrument in each ear.

Sub-portions 670 are configured as stackable structures. In some examples, sub-portions 670 are configured to mate together in a particular order. In other examples, sub-portions 670 are configured to attach together in a predefined order (e.g., dictated by a shape, structure, or function of each sub-portion 670). In some examples, electrical contacts and other physical features of each sub-portion is identical so that any sub-portion may be a top, bottom, or middle sub-portion 670.

Besides sensing, sub-portions 670 may be configured as output components that provide alerts or other feedback to a user. Sub-portions 670 may provide acoustic outputs, non-acoustic outputs such as haptic feedback, vibration, or electrical and/or neural stimulation that can be sensed by the user from surface electrodes on sub-portions 670.

Figure 7:
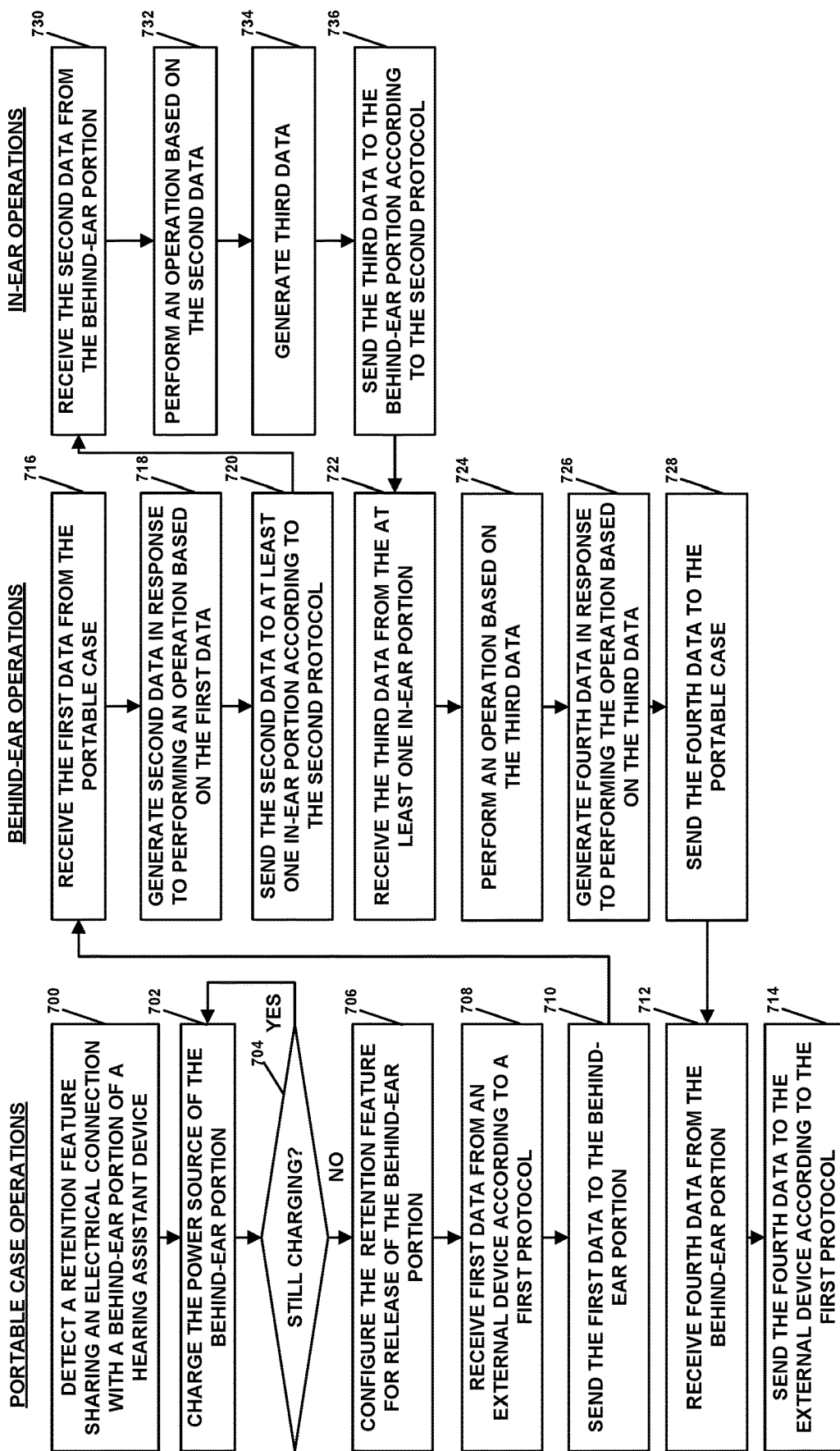
FIG. 7 is a flow chart illustrating example operations performed by an example hearing assistance system, in accordance with one or more aspects of the present disclosure.

FIG. 7 is a flow chart illustrating example operations performed by an example hearing assistance system, in accordance with one or more aspects of the present disclosure. FIG. 7 is described below in the context of system 100 of FIG. 1. System 100 may execute operations 700-736 in a different order than that shown in FIG. 7. System 100 may perform additional or fewer operations than those shown in FIG. 7. As one example, portable case 104 executes operations 700-714, behind-ear portion 106A executes operations 716-728, and in-ear portion 108 executes operations 730-736; however, system 100 may distribute the execution of operations 700-736 amongst components of system 100 in other ways.

In operation, from the perspective of portable case 104, portable case 104 may detect a retention structure sharing an electrical connection with a behind-ear portion of a hearing assistance device (700). For example, a processor of portable case 104 may determine that behind-ear portion 106B has been inserted into retention structure 112B in response to determining that the hearing assistance device charging circuitry of portable case 104 is electrically coupled to an energy source of behind-ear portion 106B.

Portable case 104 may charge a power source of the behind-ear portion (702). For example, in response to detecting the electrical connection shared between the charging circuitry of portable case 104 and behind-ear portion 106B, the processor of portable case 104 may enable the charging circuitry and cause the charging circuitry to replenish the energy source of behind-ear portion 106B with electrical energy. In some examples, portable case 104 may enable an electro-permanent magnet in retention structure 112B to cause a strong enough magnetic bond between retention structure 112B and behind-ear portion 106B that prevents a user from removing behind-ear portion 106B from retention structure 112B during the charging process.

During the charging process, portable case 104 may determine whether the power source of the behind-ear portion is charged to a specified level (e.g., fully charged to capacity) or still charging (704). In response to determining that the power source is not charged to the specified level (704, NO decision), portable case 104 may keep charging the power source of the behind-ear portion (702).

However, in response to determining that the power source is charged to the specified level (704, YES decision), portable case 104 configures the retention structure to release the behind-ear portion from the portable case (706). For example, the processor of portable case 104 may monitor the remaining energy capacity of the energy source of behind-ear portion 106B and determine whether the remaining energy capacity satisfies a threshold for indicating that the energy source is charged. In response to determining that the remaining energy capacity indicates that the energy source is charged, the processor of portable case 104 may disable the charging circuitry and cause the charging circuitry to stop replenishing the energy source of behind-ear portion 106B with electrical energy. As portable case 104 ceases charging the power source, portable case 104 may disable an electro-permanent magnet in retention structure 112B to diminish a magnetic bond between retention structure 112B and behind-ear portion 106B so as to allow a user to remove behind-ear portion 106B from retention structure 112B now that the charging process has terminated.

In a second example, portable case 104 may be configured as an audio controller that detects available audio sources and automatically connects with the mobile phone when portable case 104 detects a connection with the phone. Or portable case 104 may be configured as a gateway that enables hearing assistance device 102 to communicate according to a protocol used by computing devices 101 even though hearing assistance device 102 itself may not be configured to communicate according to that protocol.

In further operation, from the perspective of portable case 104, portable case 104 may receive, from an external computing device, first data according to a first communication protocol (708). For example, a processor of portable case 104 may communicate, via network 105, using a Wi-Fi® connection, with a music service executing at a server of computing devices 101 and receive an audio stream or some other data over the Wi-Fi® connection.

Portable case 104 may send, to a behind-ear portion of a hearing assistance device, the first data (710). For example, a processor of portable case 104 may open a communication session with behind-ear portion 106A and send the data received from the mobile phone to behind-ear portion 106A for subsequent playback via in-ear portion 108. In some examples, portable case 104 sends the first data according to the first communication protocol. For instance, portable case 104 may share a separate Wi-Fi® connection with behind-ear portion 106A and may pass the data received from the music service over the Wi-Fi® connection and on to behind-ear portion 106A for further processing.

In other examples, portable case 104 sends the first data according to a second communication protocol that is different than the first communication protocol. For instance, behind-ear portion 106A may be configured to communicate with portable case 104 via Bluetooth®, using an intra or inter body network protocol, or some other communication protocol that is different than Wi-Fi®. Portable case 104 may send the data received from the mobile phone over the connection shared with behind-ear portion 106A regardless as to the connection shared between portable case 104 and the mobile phone.

Portable case 104 may receive, from the behind-ear portion, fourth data (712). For example, behind-ear portion 106A may share log-in credentials to the music service with portable case 104 so that portable case 104 can manage the connection with the music service on behalf of hearing assistance device 102. Behind-ear portion 106A may retrieve the log-in credentials via user data stored locally at behind-ear portion 106A or may receive the log-in credentials as a user provides input to behind-ear portion 106A (e.g., a voice input with the user's user name and password).

Portable case 104 may send, to the external computing device, the second data (714). For example, portable case 104 may communicate over Wi-Fi® with the music service server to log the user into the music service so he or she can enjoy streaming music via in-ear portion 108. In some case, portable case 104 receives data from behind-ear portion 106A according to the same or different communication protocol used by portable case 104 to communicate with computing devices 101. That is, portable case 104 may receive the login credentials via Bluetooth® and share the credentials with the music service via Wi-Fi®; or in some examples, portable case 104 may receive the login credentials via Wi-Fi® and also share the credentials with the music service via Wi-Fi®.

In operation, from the perspective of behind-ear portion 106A, behind-ear portion 106A may receive first data from a portable case (716). For example, behind-ear portion 106A may receive the audio stream that portable case 104 receives from the music service executing at computing devices 101. Behind-ear portion 106A may receive the audio stream via a Bluetooth® connection or according to some other communication protocol.

Behind-ear portion 106A may generate, based on the first data, second data in response to performing an operation based on the first data (718). For example, behind-ear portion 106A may generate playback instructions for causing in-ear portion 108 to output sounds based on the music stream.

Behind-ear portion 106A may send, to at least one in-ear portion of the hearing assistance system, the second data (720). For example, behind-ear portion 106A may send the playback instructions to in-ear portion 108 and/or some other in-ear portion of a different hearing assistance device that is in communication with behind-ear portion 106A. In other words, "the at least one in-ear portion 108" may include at least one of: in-ear portion 108 or a different in-ear portion of a different hearing assistance device other than hearing assistance device 102. Behind-ear portion 106A may communicate with in-ear portion 108 (i.e., the in-ear portion 108 that is physically paired with behind-ear portion 106A) and behind-ear portion 106A may communicate with an in-ear portion of a different hearing assistance device that is not hearing assistance device 102. In this way, behind-ear portion 106A may communicate with two different in-ear portions, one in a user's left ear and one in the user's right ear.

In some examples, behind-ear portion 106A receives the first data from portable case 104 according to a first communication protocol and sends the second data to the at least one in-ear portion according to a second communication protocol. For instance, the first and second communication protocols may be different; behind-ear portion 106A may receive the audio stream via a Bluetooth® connection with portable case 104 and may transmit the playback instructions via an intra or inter body network communication protocol to in-ear portion 108. Alternatively, the first and second communication protocols may be the same; behind-ear portion 106A may receive the audio stream via a Bluetooth® connection with portable case 104 and may transmit the playback instructions via a Bluetooth® connection with in-ear portion 108.

In operation, continuing from the perspective of behind-ear portion 106A, behind-ear portion 106A may receive third data from at least one in-ear portion of the hearing assistance system (722). For example, behind-ear portion 106A may receive information from in-ear portion 108 about sounds being picked up by a microphone of in-ear portion 108. In some examples, the at least one in-ear portion of the hearing assistance system includes at least one of: in-ear portion 108 or an in-ear portion of a different hearing assistance device that is not hearing assistance device 102.

Behind-ear portion 106A may perform an operation based on the first data (724). For example, an advanced noise-cancelling algorithm executing at behind-ear portion 106A may process the sound information received from in-ear portion 108 to remove noise or otherwise enhance spoken dialogue identified from the sound information.

Behind-ear portion 106A may generate fourth data in response to performing the operation based on the first data (726). For example, behind-ear portion 106A may create audio data representative of the processed sound information for subsequent playback.

Behind-ear portion 106A may send, to a portable case of the hearing assistance system, the second data generated in response to performing the operation based on the first data (728). For example, behind-ear portion 106A may send the processed audio data to portable case 104 for storing the audio data as a sound file in a memory of portable case 104. Or in some examples, behind-ear portion 106A may cause a speaker of in-ear portion 108 to output sound based on the processed audio data so that what a user hears via in-ear portion 108 is the processed, filtered, enhanced sound, rather than the raw noisy audio picked up by the microphone.

Of course, it should be understood that in some examples, behind-ear portion 106A communicates with portable case 104 and in-ear portion 108 using a same communication protocol. And in other cases, behind-ear portion 106A communicates with portable case 104 and in-ear portion 108 using different communication protocols—communicating with portable case 104 via a protocol such as Bluetooth® and communicating with in-ear portion 108 via a protocol that is more suitable for intra or inter body communications, such as an intra or inter body network protocol.

In operation, from the perspective of in-ear portion 108, in-ear portion 108 may receive, from a behind-ear portion of the hearing assistance device, second data (730). For example, in-ear portion 108 may receive playback instructions that behind-ear portion 106A generates from a music stream.

In-ear portion 108 may perform an operation based on the first data (732). For example, in-ear portion 108 may generate output via a speaker or other output component to convey sounds being interpreted by behind-ear portion 106A from the music stream.

In continuing operations from the perspective of in-ear portion 108, in-ear portion 108 may generate third data (734). For example, a microphone of in-ear portion 108 may pick up sounds in a user's environment and may generate audio data representative of the sounds.

In-ear portion 108 may send, to the behind-ear portion, the third data (736). For example, in-ear portion 108 may transmit an indication of the audio data to behind-ear portion 106A for causing behind-ear portion 106A to perform advanced audio enhancement of the sounds in the user's environment. For example, behind-ear portion 106A may isolate human dialogue from the sounds or may determine a context from the sounds and an assistant executing at behind-ear portion 106A may recommend the user perform a particular action associated with the sound or context. For instance, the assistant may determine that the user is at a sporting event and may recommend that the user listen to a radio broadcast of the event in at least one ear, rather than listen to the live audio being picked up by in-ear portion 108 in both ears.

FIGS. 8A through 8C are conceptual diagrams illustrating some example retention structure arrangements of a portable case for storing and charging behind-ear portions of an example hearing assistance device, in accordance with one or more aspects of the present disclosure. In the examples of FIGS. 8A through 8C, various arrangements of retention structures 812A-812G (collectively referred to herein as "retention structures 812").

FIG. 8A shows a circumferential arrangement of retention structures 812 around the circumference of housing 804A. In other words, each of retention structures 812 may be in a different circumferential position of housing 804A. Put another way, each circumferential position of housing 804A may correspond to a different angular positions about a center of housing 804A. The different circumferential positions may be equally spaced around the circumference of housing 804A or may be unequally spaced and grouped near one or more sectors of the circumference of housing 804A.

FIG. 8B shows a linear arrangement of retention structures 812 around the circumference of housing 804B. That is, each of retention structures 812 may be in a different position in-line with a linear axis of housing 804B. Said differently, retention structures 812 may form a linear arrary, row, column of retention structures 812 at different linear positions along a linear axis of the housing. The different linear positions may be uniformly spaced along a linear axis of housing 804B or may be unequally spaced and grouped near different portions of the linear axis of housing 804B.

FIG. 8C shows a diagonal-linear or square arrangement of retention structures 812 of housing 804C. Each of retention structures 812 may be in a different corner of housing 804B. Groups of one or more retention structures 812 may be uniformly distributed amongst the corners of housing 804B. Or in some cases, only some of the corners of housing 804B include one or more retention structures 812.

FIGS. 9A through 9D are conceptual diagrams illustrating example behind-ear portions of an example hearing assistance device, in accordance with one or more aspects of the present disclosure. Behind-ear portions 906A, 906B, 906C, and 906D of FIGS. 9A through 9D are examples of behind-ear portions 106, 206, 406, and 606 of FIGS. 1, 2A through 2D, 4, and 6A through 6C and are described in the context of the preceding figures.

Behind-ear portions 906A through 906D (collectively "behind-ear portions 906") are example behind-ear portions formed of stackable sub-portions 970A-970E (collectively "sub-portions 970). Although each of behind-ear portions 906 is shown as having between three and five separate sub-portions 970, in other examples, behind-ear portions 906 have more or fewer sub-portions 970 than shown.

Each sub-portion 970 mates with another sub-portion 970 via one or more contacts and attachment features, including mechanical, magnetic, and electro-magnetic. Each sub-portion 970 may provide a specific functionality. Each of sub-portions 970 may be swappable for a different sub-portion. The individual components of behind-ear portion 408 shown in FIG. 4 may be distributed amongst different sub-portions 970. By mixing and matching various types of sub-portions 970, a user can customize each of behind-ear portions 906 for a particular situation. As one example, sub-portion 970A may be a rechargeable power source, sub-portion 970B may be processing circuitry, sub-portion 970C may be a microphone, sub-portion 970D may be a data storage device, and sub-portion 970E may be a wireless radio.

In one example, behind-ear portion 906A includes each of sub-portions 970A through 970E arranged in a particular order. In another example, behind-ear portion 906B includes each of sub-portions 970A through 970E arranged in a different order than the order of sub-portions 970 of behind-ear portion 906A.

In another example, behind-ear portion 906C includes sub-portions 970B, 970A, 970C, and 970E arranged in that order. In another example, behind-ear portion 906D includes sub-portion 970C, sub-portion 970B, and sub-portion 970A arranged in that order.

FIGS. 9A through 9D show that many different combinations of one or more sub-portions 970 may be used to form a behind-ear portion, such as behind-ear portions 906. In this way, a user can tailor or customize his or her left and right side hearing assistance devices in various unique ways, depending on his or her needs for a particular situation.

FIGS. 10A through 10G are conceptual diagrams illustrating an example sequence for swapping out a behind-ear portion of an example hearing assistance device for a different behind-ear portion that is seated in an example portable, in accordance with one or more aspects of the present disclosure. The components shown in FIGS. 10A through 10G are examples of the components shown in the preceding figures and are described in the context of the preceding figures. The example shown in FIGS. 10A through 10G shown a sequence of steps that a user may perform to swap out behind-ear portion 1006A in exchange for behind-ear portion 1006B which is shown seated in portable case 1004.

Figure 10A:
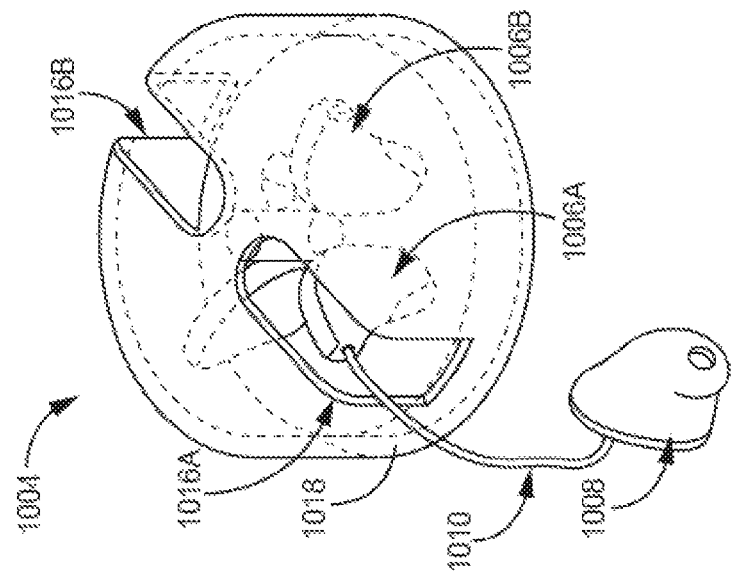
FIGS. 10A through 10G are conceptual diagrams illustrating an example sequence for swapping out a behind-ear portion of an example hearing assistance device for a different behind-ear portion that is seated in an example portable, in accordance with one or more aspects of the present disclosure.
Figure 10B:
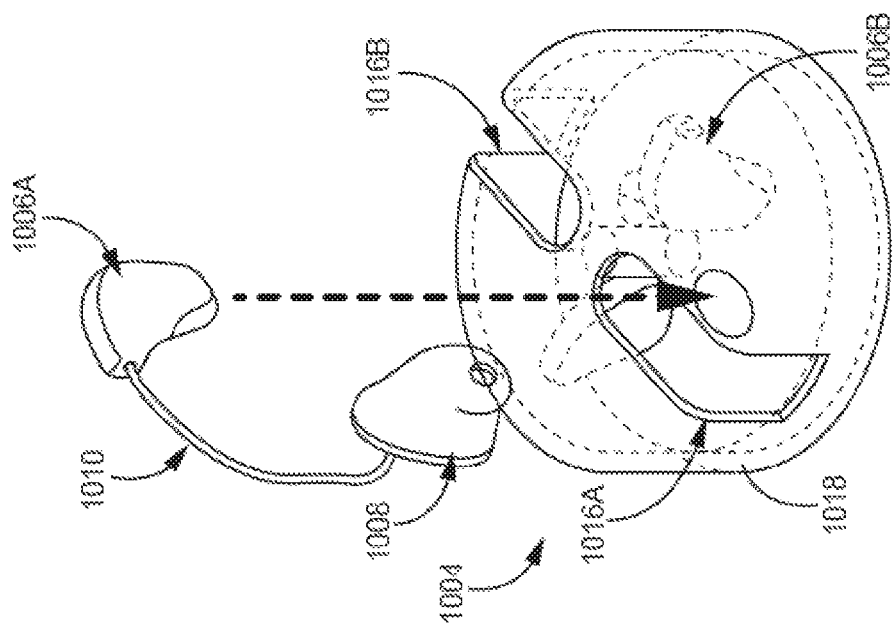

FIG. 10A includes portable case 1004 including cover 1018 having openings 1016A and 1016B. A user, while holding tether 1010 and/or in-ear portion 1008, may position behind-ear portion 1006A over opening 1016A and place behind-ear portion 1006A in the retention structure exposed via opening 1016A. FIG. 10B shows behind-ear portion 1006A having been placed in the retention structure exposed via opening 1016A. After placing behind-ear portion 1006A in the retention structure exposed via opening 1016A, FIG. 10C shows that the user may pull, twist, or otherwise detach tether 1010 from behind-ear portion 1006A.

Figure 10D:
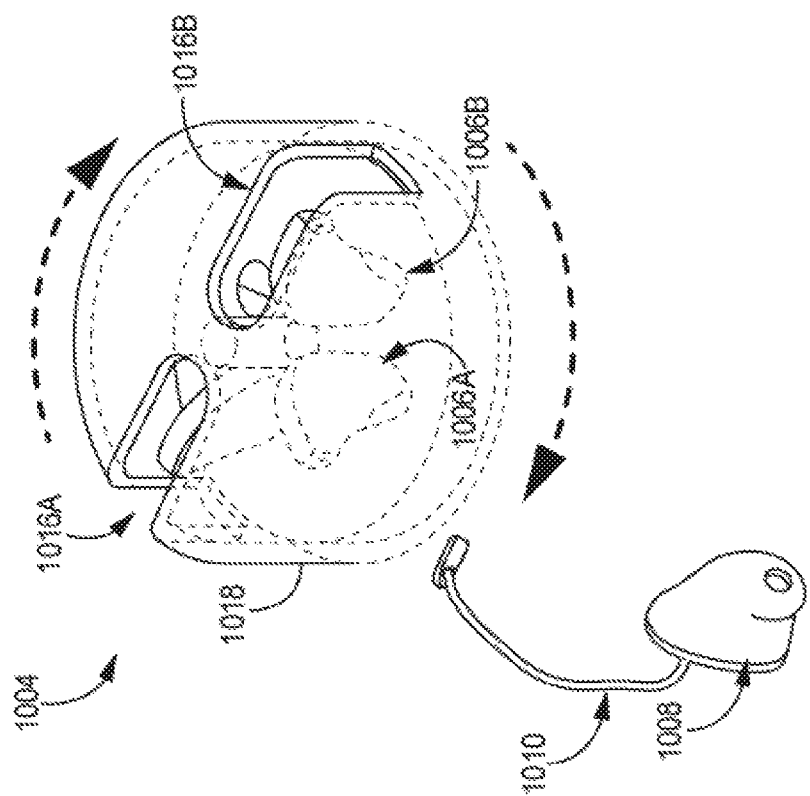
Figure 10C:
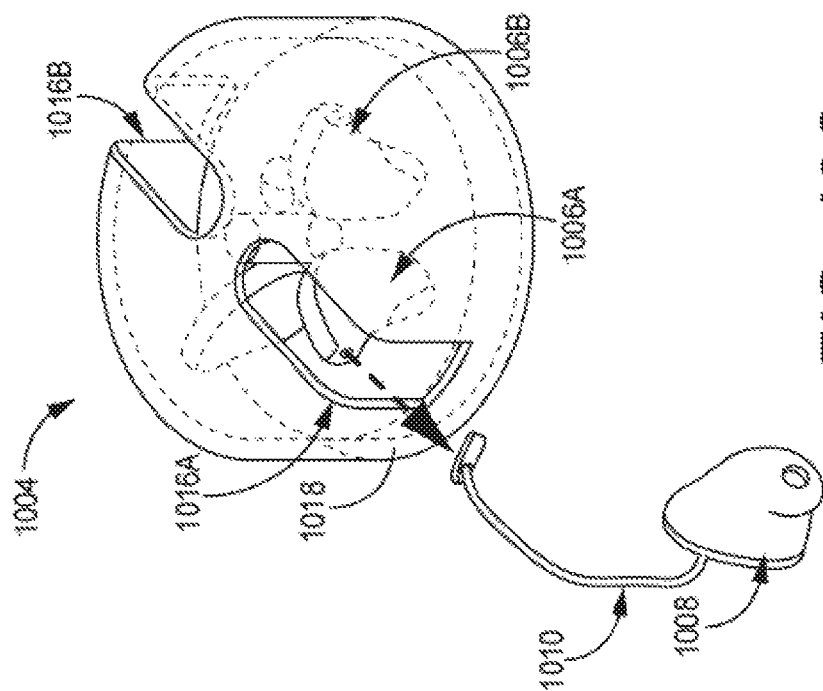
Figure 10F:
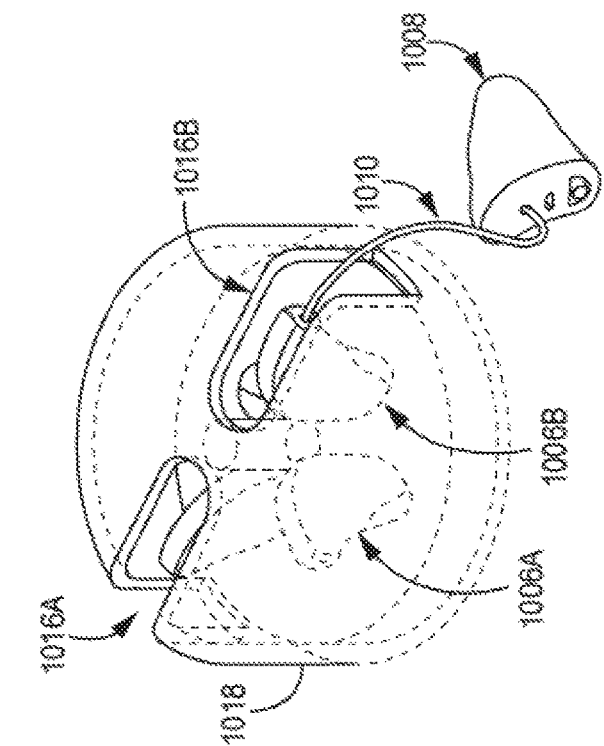
Figure 10E:
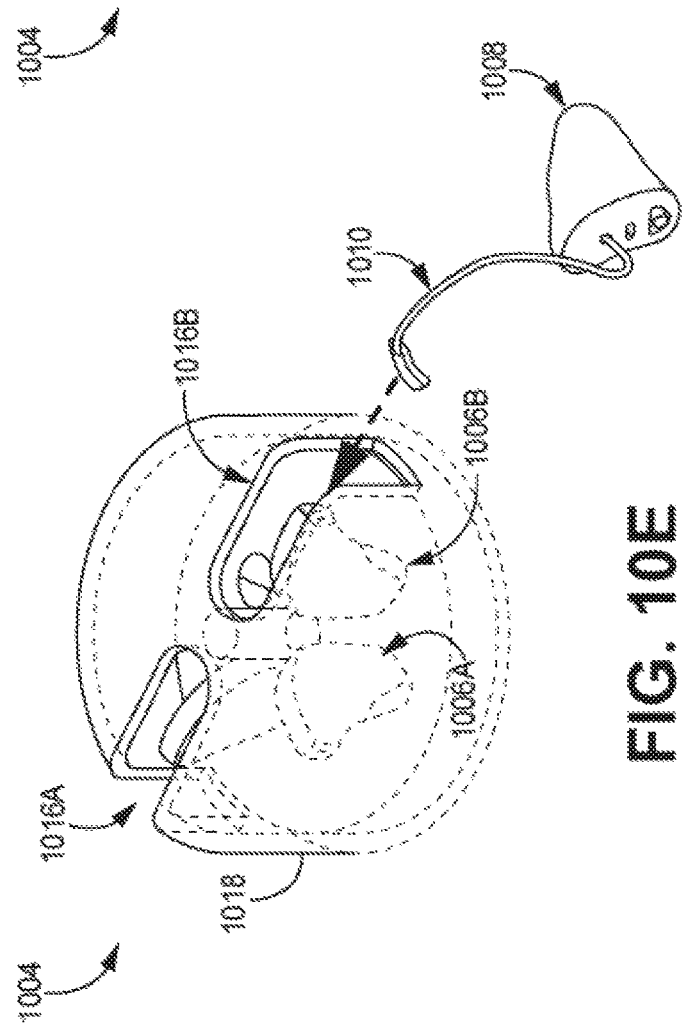
Figure 10G:
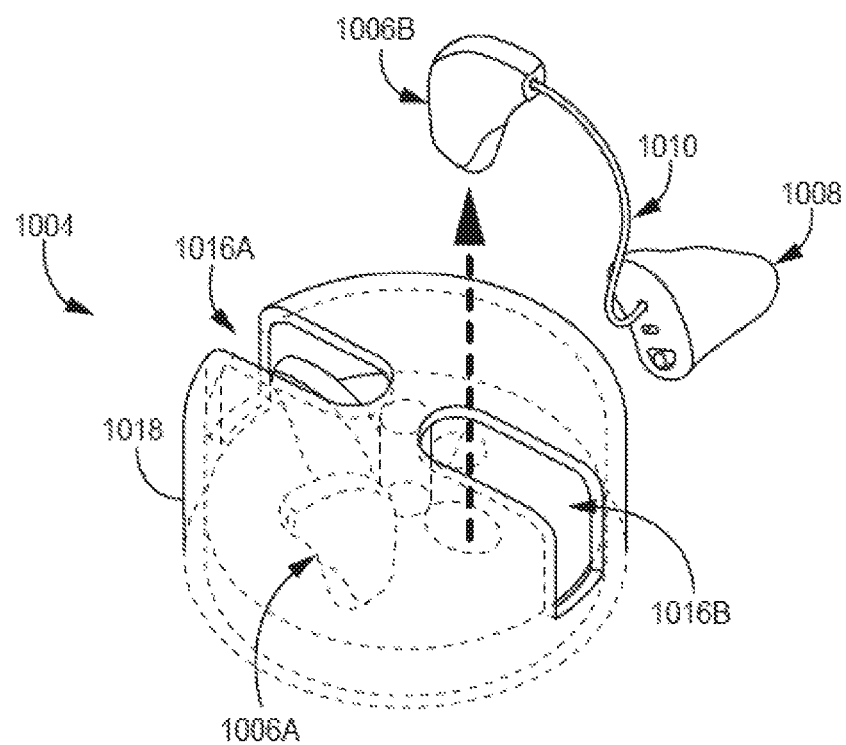

As shown in FIG. 10D, the user may manipulate cover 1018 of portable case 1004 so that opening 1016B exposes the retention structure holding behind-ear portion 1006A. After revealing behind-ear portion 1006B by manipulating cover 1018, FIG. 10E shows that the user may move tether 1010 towards behind-ear portion 1006B. FIG. 10F shows the user attaching tether 1010 to behind-ear portion 1006B. Finally, FIG. 10G shows the user removing behind-ear portion 1006B from portable case 1004 by holding tether 1010 and pulling behind-ear portion 1006B, tether 1010, and in-ear portion 1008 as a single hearing assistance device.

Figure 11:
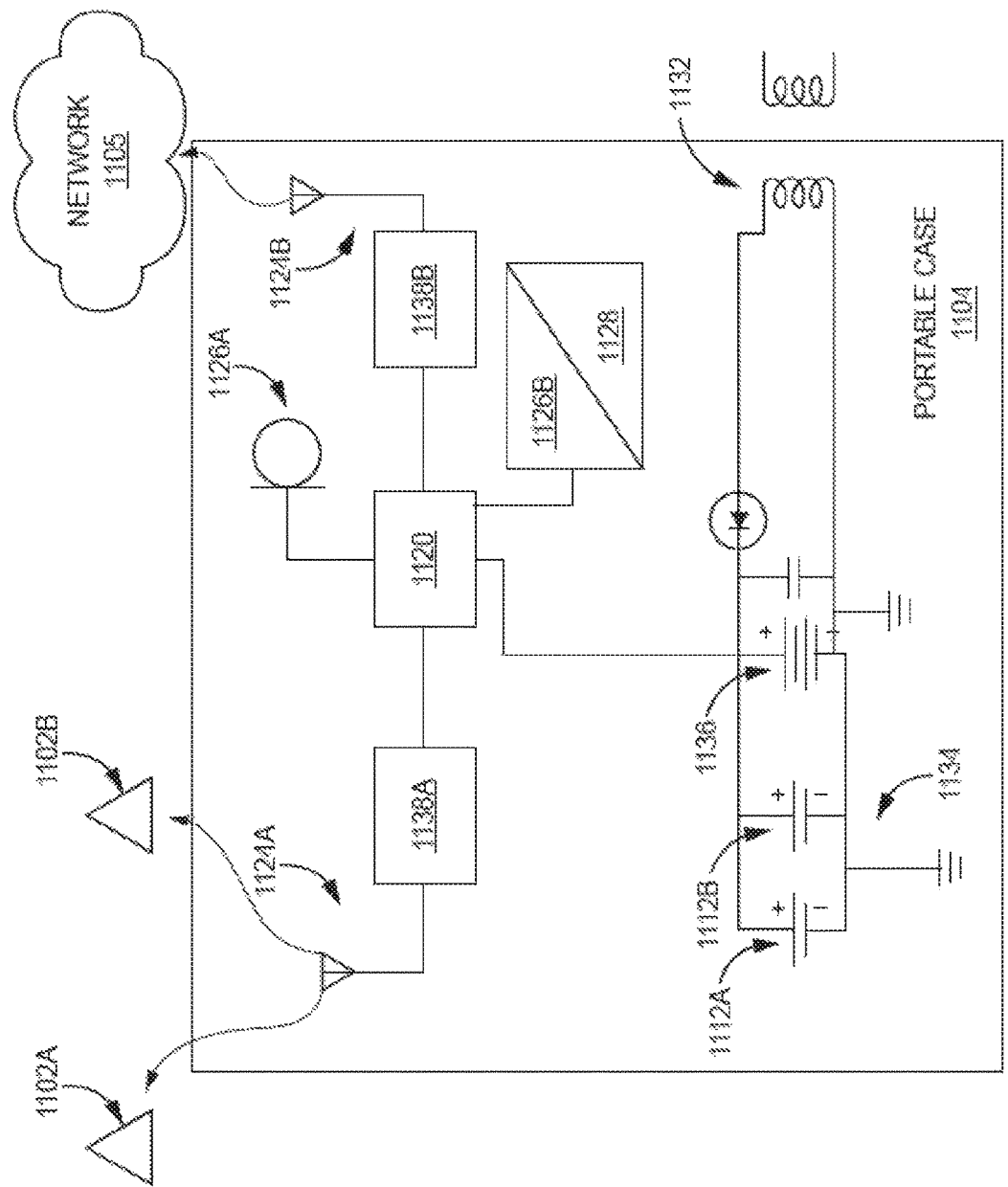
FIG. 11 is a schematic illustrating an example portable case for storing and charging behind-ear portions of an example hearing assistance device, in accordance with one or more aspects of the present disclosure.

FIG. 11 is a schematic illustrating an example portable case for storing and charging behind-ear portions of an example hearing assistance device, in accordance with one or more aspects of the present disclosure. FIG. 11 is described in the context of FIG. 3 and the other preceding figures.

Portable case 1104 is an example of portable case 304 of FIG. 3. In some examples, portable case 1104 is configured to communicate with remote computing devices (e.g., computing devices 101) via network 1105. In some examples, portable case 1104 is configured to communicate directly with hearing assistance devices 1102A and 1102B. Whether communicating via network 1105 or communicating directly with hearing assistance devices 1102A and 1102B, portable case 1104 relies on communication units 1138A and 1138B to exchange information between portable case 1104 and the other devices. In some examples, communication units 1138A and 1138B are transceivers. In some examples, communication units 1138A and 1138B are a single component or multiple components, as shown in FIG. 11. Also included in portable case 1104 are two antennas 1124A and 1124B. Antennas 1124A and 1124B may include a single antenna or multiple antennas. Antennas 1124A and 1124B may be two different types of antennas.

Portable case 1104 includes one or more processors 1120 for controlling the operations of portable case 1104. Processors 1120 may include one or more hardware processing units, software processing units, or a combination of hardware, software, and/or firmware for controlling the operations of portable case 1104.

Portable case further includes a user interface unit that includes one or more input components 1126B and one or more output components 1126. The user interface of portable case 1104 may perform operations described above with respect to UI module 320 and other components of portable case 304 of FIG. 3 for providing output to a user and receiving input from the user.

Portable case 1104 may include microphone 1126A. Microphone 1126A may be configured as a remote microphone for obtaining audio in the surroundings of portable case 1104. In some examples, microphone 1126A detects voice input as part of a voice-controlled user interface of portable case 1104.

For charging behind-ear portions of example hearing assistance devices, portable case 1104 includes retention structures 1112A and 1112B which are operatively coupled to HAD charger 1134. Portable case 1104 also includes energy storage 1136 which is charged by system charger 1132. System charger 1132 may be a wireless charging component relying on transformer. In other examples, system charger 1132 is a wired charging component or a combination of wired and wireless charging circuitry. In any event, portable case 1104 is configured to charge one or more behind-ear portions of an example hearing assistance device using the electrical energy stored by energy storage 1136 and output via HAD 1134.

FIGS. 12A through 12D are conceptual diagrams illustrating various arrangements of retention structures of an example portable case, in accordance with one or more aspects of the present disclosure. FIG. 12A through 12D are described in the context of the preceding figures.

Figure 12A:
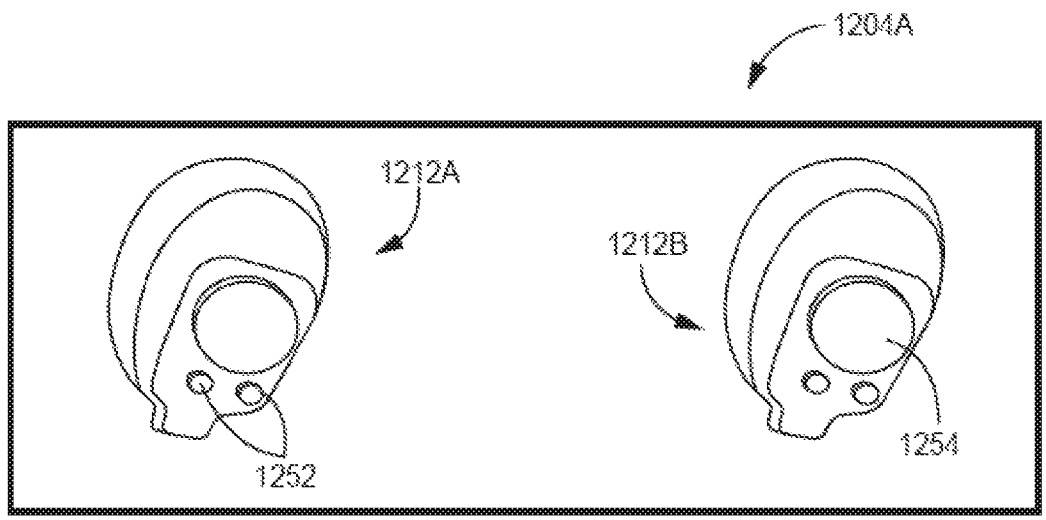
FIGS. 12A through 12D are conceptual diagrams illustrating various arrangements of retention structures of an example portable case, in accordance with one or more aspects of the present disclosure.

FIG. 12A shows portable case 1204A with empty retention structures 1212A and 1212B in a linear arrangement. Contacts 1252 and 1254 are present in both retention structures 1212A and 1212B. Contacts 1252 are similar to contacts 552 of FIG. 5. Contacts 1254 are similar to contacts 554 of FIG. 5

Figure 12B:
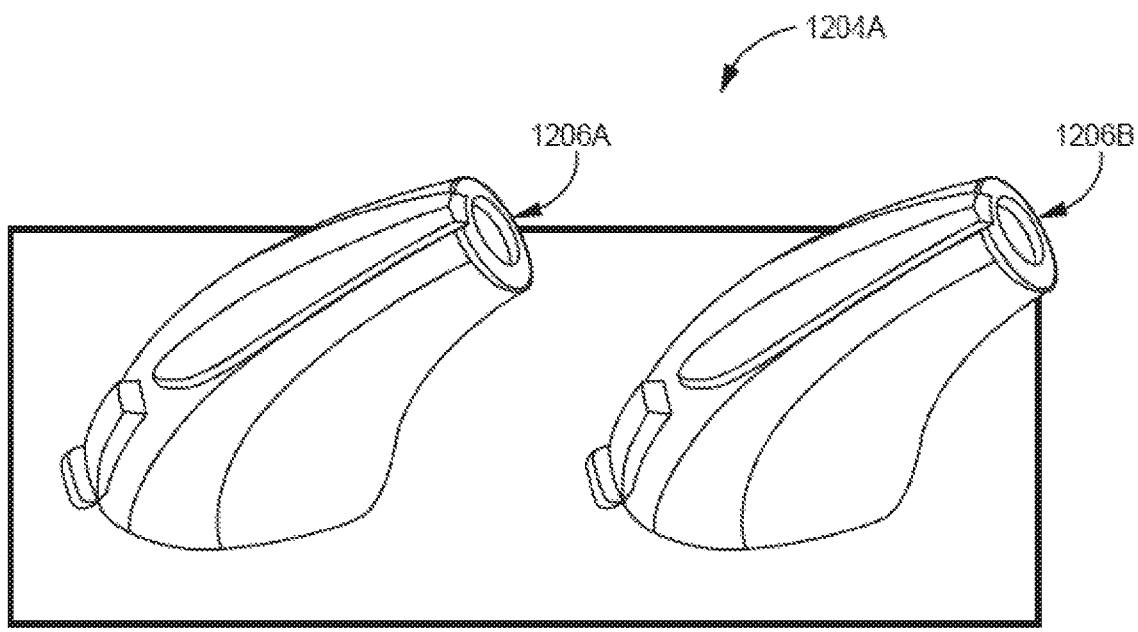
Figure 12D:
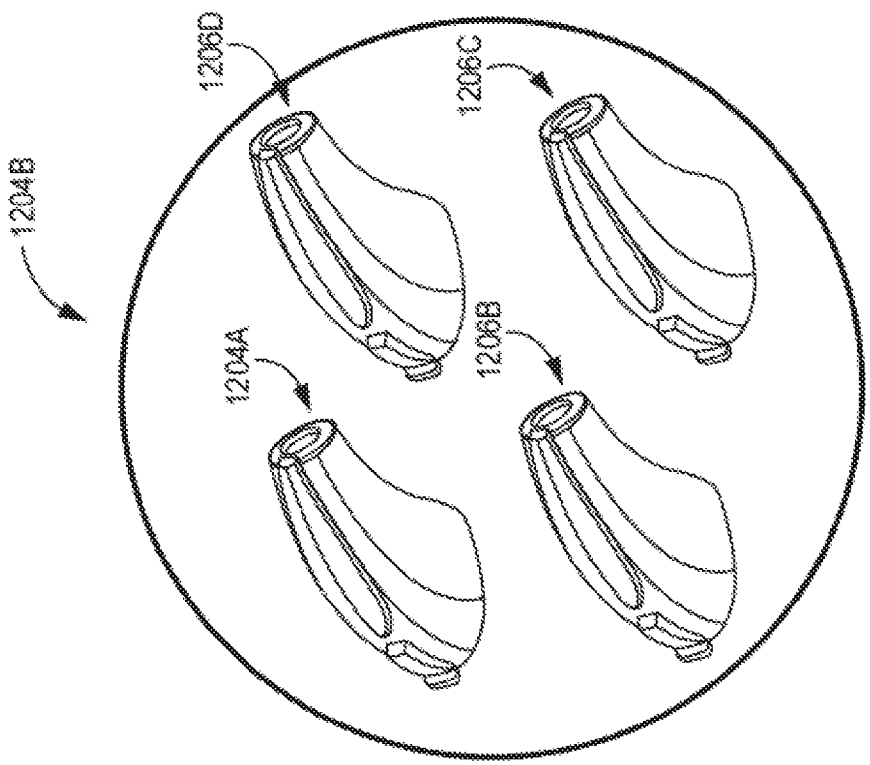

FIG. 12B shows portable case 1204A with full retention structures 1212A and 1212B. That is, behind-ear portions 1206A and 1206B mate with respective contacts 1252 and 1254 that are present in a respective one of retention structures 1212A and 1212B and are (mechanically and/or magnetically) held in place by the respective one of retention structures 1212A and 1212B.

Figure 12C:
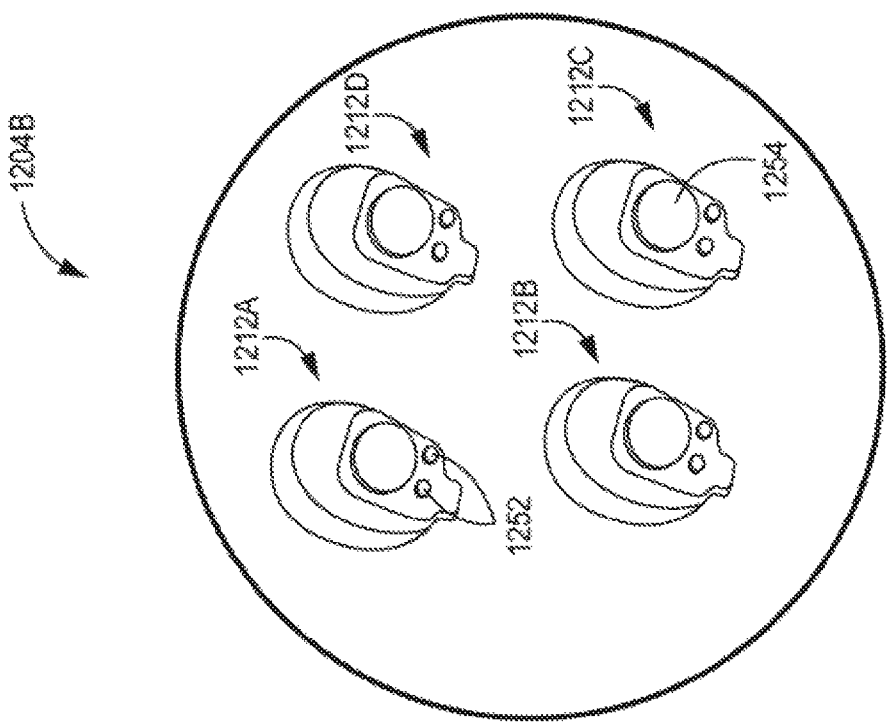

FIG. 12C shows portable case 1204B with empty retention structures 1212A through 1212D in a circular arrangement. Contacts 1252 and 1254 are present in each of retention structures 1212A through 1212D. Contacts 1252 are similar to contacts 552 of FIG. 5. Contacts 1254 are similar to contacts 554 of FIG. 5

FIG. 12B shows portable case 1204B with full retention structures 1212A through 1212D. That is, behind-ear portions 1206A through 1206D mate with respective contacts 1252 and 1254 that are present in a respective one of retention structures 1212A through 1212D and are (mechanically and/or magnetically) held in place by the respective one of retention structures 1212A through 1212D.

Example 1

A portable case for storing and charging hearing assistance devices, the portable case comprising: at least one retention structure configured to retain at least part of a hearing assistance device; an energy storage device; charging circuitry electrically coupled to the energy storage device and the at least one retention structure; at least one processor configured to: detect when the at least one retention structure shares an electrical connection with the at least part of the hearing assistance device that is retained by the at least one retention structure; and cause the charging circuitry to charge, via the electrical connection shared by the at least one retention structure and the at least part of the hearing assistance device, a power source of the hearing assistance device.

Example 2

The portable case of example 1, wherein the at least one retention structure comprises two or more retention structures, wherein each retention structure of the two or more retention structures is configured to retain at least part of a single hearing assistance device at a time.

Example 3

The portable case of any of examples 1-2, wherein the portable case comprises a housing and the two or more retention structures are arranged at different circumferential positions in the housing.

Example 4

The portable case of any of examples 1-3, wherein the portable case comprises a housing and the two or more retention structures are arranged linearly in the housing.

Example 5

The portable case of any of examples 1-4, wherein the portable case comprises a housing and a cover, and wherein an opening of the at least one retention structure is concealable by the cover.

Example 6

The portable case of example 5, wherein the cover is configured to reveal the opening of the at least one retention structure after mechanical manipulation of the cover.

Example 7

The portable case of example 6, where the cover is configured to reveal the opening of the at least one retention structure after rotating the cover.

Example 8

The portable case of any of examples 6-7, where the cover is configured to reveal the opening of the at least one retention structure after sliding the cover.

Example 9

The portable case of any of examples 6-8, where the cover is configured to reveal the opening of the at least one retention structure after detaching the cover.

Example 10

The portable case of any of examples 6-9, wherein the at least one retention structure comprises two or more retention structures, and the cover is configured to reveal a single retention structure of the two or more retention structures after mechanical manipulation of the cover.

Example 11

The portable case of any of examples 1-10, wherein the at least one retention structure comprises an electro-permanent magnet, and the at least one processor is further configured to control circuitry to strengthen a magnetic connection between the electro-permanent magnet and the at least part of the hearing assistance device that is retained by the at least one retention structure while causing the charging circuitry to charge the power source of the hearing assistance device.

Example 12

The portable case of any of examples 1-11, wherein the at least one processor is further configured to cause the charging circuitry to cease charging the power source of the hearing assistance device in response to determining when the power source of the hearing assistance device is charged to a specified level.

Example 13

The portable case of example 12, wherein the at least one retention structure comprises an electro-permanent magnet, and the at least one processor is further configured to control circuitry to weaken a magnetic connection between the electro-permanent magnet and the at least part of the hearing assistance device that is retained by the at least one retention structure after causing the charging circuitry to cease charging the power source of the hearing assistance device.

Example 14

The portable case of any of examples 12-13, wherein the at least one retention structure comprises one or more mechanical features that are configured to eject the at least part of the hearing assistance device that is retained by the at least one retention structure after the magnetic connection between the electro-permanent magnet and the at least part of the hearing assistance device is weakened.

Example 15

The portable case of any of examples 1-14, wherein the at least one retention structure includes one or more attachment features configured to mate with corresponding attachment features of the at least one part of the hearing assistance device.

Example 16

The portable case of example 15, wherein the one or more attachment features include at least one of mechanical features, magnetic features, or electro-magnetic features.

Example 17

The portable case of any of examples 15-16, wherein the one or more attachment features include two or more electrical contacts configured to conduct electrical current between the energy storage device and the at least part of the hearing assistance device.

Example 18

The portable case of any of examples 1-17, further comprising one or more communication units configured to exchange information between the portable case and one or more external devices.

Example 19

The portable case of example 18, wherein the one or more external devices include: a computing device, the hearing assistance device, or at least one other hearing assistance device.

Example 20

The portable case of any of examples 18-19, wherein the one or more communication units are configured for wireless communication between the portable case and the one or more external devices

Example 21

The portable case of any of examples 18-20, wherein the one or more communication units are configured for wired communication between the portable case and the one or more external devices.

Example 22

The portable case of any of examples 18-21, wherein the one or more communication units include at least one of: near field communication radio, a Bluetooth® radio, a Wi-Fi® radio, a cellular radio, a software defined radio, a multimodal radio, a near field magnetic induction radio, or a radio configured to communicate via a wireless intra or inter body-network protocol.

Example 23

The portable case of any of examples 18-22, wherein at least one processor is further configured to: receive, via the one or more communication units, first data from a first external device of the one or more external devices, the first data being encoded according to a first communication protocol; after decoding the first data, generate second data, the second data being encoded according to a second communication protocol; and send, via the one or more communication units, the second data to a second external device of the one or more external devices that is different than the first external device.

Example 24

The portable case of example 23, wherein: the hearing assistance device is a first hearing assistance device; the first external device is the first hearing assistance device; the second external device is a second hearing assistance device; and the first communication protocol and the second communication protocol are a wireless intra or inter body network protocol.

Example 25

The portable case of any of examples 23-24, wherein: the first external device is the hearing assistance device; the second external device is a mobile computing device; the first communication protocol is a wireless intra or inter body network protocol; and the second communication protocol is a second wireless communication protocol.

Example 26

The portable case of any of examples 23-25, wherein the first data and the second data comprise an audio data stream.

Example 27

The portable case of any of examples 18-26, wherein the at least one processor is further configured to execute, based on the information exchanged between the portable case and one or more external devices, one or more operations on behalf of the one or more external devices.

Example 28

The portable case of any of examples 1-27, further comprising a microphone, wherein the at least one processor is configured to wirelessly transmit audio captured using the microphone to one or more external devices.

Example 29

The portable case of any of examples 1-28, further comprising:
one or more input components configured to detect user inputs as part of a user interface.

Example 30

The portable case of example 29, wherein the one or more input components comprise an inertial measurement configured to detect user gestures performed while holding the portable case.

Example 31

The portable case of any of examples 29-30, wherein the one or more input components comprise a microphone configured to detect voice commands.

Example 32

The portable case of any of examples 29-31, wherein the one or more input components comprise a presence-sensitive input component configured to detect touch inputs.

Example 33

The portable case of any of examples 1-32, further comprising:
one or more output components configured to generate outputs of a user interface.

Example 34

The portable case of example 33, wherein the one or more output components comprise one or more of a display, a speaker, or a haptic feedback component configured to present the user interface.

Example 35

The portable case of any of examples 1-34, further comprising a computer-readable storage medium.

Example 36

The portable case of example 35, wherein the computer-readable storage medium is removable.

Example 37

The portable case of any of examples 35-36, wherein the computer-readable storage medium stores instructions of one or more application programs that are executable by the at least one processor.

Example 38

The portable case of example 37, wherein the computer-readable storage medium stores user data accessed by the one or more application programs when executing at the at least one processor.

Example 39

The portable case of any of examples 1-38, further comprising system charging circuitry configured to charge the energy storage device via a wired or wireless connection with an energy source.

Example 40

A hearing assistance device comprising: a behind-ear portion comprising a rechargeable energy source; an in-ear portion comprising one or more components including: at least one processor, a microphone, and a speaker; and a tether configured to transmit electrical energy from the rechargeable energy source to the one or more components of the in-ear portion.

Example 41

The hearing assistance device of example 40, wherein the in-ear portion is permanently attached to the tether.

Example 42

The hearing assistance device of any of examples 40-41, wherein an attachment feature of the in-ear portion is configured to couple to a corresponding attachment feature of the tether.

Example 43

The hearing assistance device of any of examples 40-42, wherein an attachment feature of the behind-ear portion comprises an attachment feature configured to couple to a corresponding attachment feature of the tether.

Example 44

The hearing assistance device of example 43, wherein the attachment feature of the behind-ear portion comprises at least one of mechanical features, magnetic features, or electro-magnetic features.

Example 45

The hearing assistance device of any of examples 40-44, wherein the one or more attachment features include two or more electrical contacts configured to conduct, via the tether, electrical current between the rechargeable energy source of the behind-ear portion and the one or more components of the in-ear portion.

Example 46

The hearing assistance device of any of examples 40-45, wherein two or more electrical contacts are configured to conduct electrical current between the rechargeable energy source of the behind-ear portion and charging circuitry of a portable case.

Example 47

The hearing assistance device of any of examples 40-46, wherein the in-ear portion is configured to generate sound for hearing by a user.

Example 48

The hearing assistance device of any of examples 40-46, when the in-ear portion comprises an internal energy source.

Example 49

The hearing assistance device of example 48, wherein the in-ear portion is configured to generate sound for hearing by the user when disconnected from the tether.

Example 50

The hearing assistance device of any of examples 40-49, wherein the behind-ear portion comprises at least one of a sensor, a microphone, or a communication radio configured to receive input.

Example 51

The hearing assistance device example 50, wherein the behind-ear portion is configured to operate as one or more of: a remote microphone unit that outputs audio data detected by the microphone; a remote sensor unit that outputs sensor data detected by the sensor; or a communication radio unit that outputs radio data detected by the communication radio unit.

Example 52

The hearing assistance device of example 51, wherein the behind-ear portion is configured to operate as the one or more of the remote microphone unit, the remote sensor unit, or the communication radio unit, when the behind-ear portion is detached from the tether Example 53

The hearing assistance device of any of examples 51-52, wherein the behind-ear portion is configured to communicate wirelessly with an external computing device.

Example 54

The hearing assistance device of any of examples 51-53, wherein the external computing device includes a portable case, a mobile phone, or another hearing assistance device.

Example 55

The hearing assistance device of any of examples 40-54, wherein the behind-ear portion comprises two or more sub-portions operatively coupled to the tether and the in-ear portion, each of the two or more sub-portions is stackable with and detachable from each other sub-portion from the two or more sub-portions.

Example 56

The hearing assistance device of example 55, wherein a single sub-portion of the two or more sub-portions contains the rechargeable energy source.

Example 57

The hearing assistance device of any of examples 55-56, wherein each sub-portion of the two or more sub-portions is unique in at least one function or structure with respect to each other sub-portion from the two or more sub-portions.

Example 58

The hearing assistance device of any of examples 55-57, wherein each sub-portion of the two or more sub-portions is physically distinct from each other sub-portion from the two or more sub-portions.

Example 59

The hearing assistance device of example 58, wherein each sub-portion of the one or more sub-portions is operatively coupled to at least one other sub-portion from the one or more sub-portions.

Example 60

The hearing assistance device of example 59, wherein two or more sub-portions are operatively coupled together via corresponding attachment features comprising mechanical, magnetic, or a combination of mechanical and magnetic contacts.

Example 61

The hearing assistance device of any of examples 55-60, wherein each sub-portion of the one or more sub-portions is configured to operate independently without being coupled to the in-ear portion.

Example 62

A hearing assistance system comprising: the portable case of any one of any of examples 1-39; and the hearing assistance device of any one of any of examples 40-61.

Example 63

The hearing assistance system of example 62, wherein the hearing assistance device of example 56 is a first hearing assistance device, the system further comprising a second hearing assistance device of any one of any of examples 40-61 that is communicatively coupled to the first hearing assistance device.

Example 64

The hearing assistance system of example 63, wherein the first hearing assistance device comprises at least one input component that is different than each input component of the second hearing assistance device, and the second hearing assistance device is configured to receive, from the first hearing assistance device, information obtained by the at least one input component.

Example 65

The hearing assistance system of example 64, wherein the at least one input component includes a sensor, a microphone, or a radio.

Example 66

The hearing assistance system of any of examples 63-65, wherein a behind-ear portion of first hearing assistance device comprises a combination of two or more sub-portions that is different than a combination of two or more sub-portions of the second hearing assistance device.

Example 67

A method comprising: detecting, by a portable case of a hearing assistance system, a retention structure of the portable case sharing an electrical connection with a behind-ear portion of a hearing assistance device of the hearing assistance system; charging, by the portable case, a power source of the behind-ear portion; determining, by the portable case, whether the power source of the behind-ear portion is charged; in response to determining that the power source is charged to a predetermined charging level, ceasing, by the portable case, charging the power source; and configuring, by the portable case, the retention structure to release the behind-ear portion from the portable case.

Example 68

A method comprising: receiving, by a portable case of a hearing assistance system, from an external computing device, first data according to a first communication protocol; sending, by the portable case, to a behind-ear portion of a hearing assistance device of the hearing assistance system, the first data; receiving, by the portable case, from the behind-ear portion, second data; and sending, by the portable case, to the external computing device, the second data.

Example 69

The method of example 68, wherein sending the first data comprises sending, by the portable case, to the behind-ear portion, the first data according to the first communication protocol.

Example 70

The method of example 69, wherein receiving the second data comprises receiving, by the portable case, from the behind-ear portion, the second data according to the first communication protocol.

Example 71

The method of any of examples 68-70, wherein sending the first data comprises sending, by the portable case, to the behind-ear portion, the first data according to a second communication protocol that is different than the first communication protocol.

Example 72

The method of example 71, wherein receiving the second data comprises receiving, by the portable case, from the behind-ear portion, the second data according to the second communication protocol.

Example 73

A method comprising: receiving, by a behind-ear portion of a hearing assistance device of a hearing assistance system, from a portable case of the hearing assistance system, first data; and generating, by the behind-ear portion, based on the first data, second data in response to performing an operation based on the first data.

Example 74

The method example 73, further comprising: sending, by the behind-ear portion, to at least one in-ear portion of the hearing assistance system.

Example 75

The method of example 74, wherein the at least one in-ear portion of the hearing assistance system includes at least one of: an in-ear portion of the hearing assistance device or an in-ear portion of a different hearing assistance device.

Example 76

The method of any of examples 74-75, wherein: the first data is received according to a first communication protocol; and the second data is sent according to a second communication protocol.

Example 77

The method of example 76, wherein the first communication protocol and the second communication protocol are corresponding communication protocols.

Example 78

The method of any of examples 76-77, wherein the first communication protocol and the second communication protocol are different communication protocols.

Example 79

A method comprising: receiving, by a behind-ear portion of a hearing assistance device of a hearing assistance system, from at least one in-ear portion of the hearing assistance system, first data; and performing, by the behind-ear portion, an operation based on the first data.

Example 80

The method of example 79, wherein the at least one in-ear portion of the hearing assistance system includes at least one of: an in-ear portion of the hearing assistance device or an in-ear portion of a different hearing assistance device.

Example 81

The method of any of examples 79-80, further comprising: sending, by the behind-ear portion, to a portable case of the hearing assistance system, fourth data generated in response to performing the operation based on the first data.

Example 82

The method of example 80, wherein: the first data is received according to a first communication protocol; and the second data is sent according to a second communication protocol.

Example 83

The method of example 82, wherein the first communication protocol and the second communication protocol are corresponding communication protocols.

Example 84

The method of any of examples 82-83, wherein the first communication protocol and the second communication protocol are different communication protocols.

Example 85

A method comprising: receiving, by an in-ear portion of a hearing assistance device of a hearing assistance system, from a behind-ear portion of the hearing assistance device, first data; performing, by the in-ear portion, an operation; generating, by the in-ear portion, second data in response to performing the operation; and sending, by the in-ear portion, to the behind-ear portion, the second data.

Example 86

The method of example 85, wherein the first data is received, and the second data is sent, according to a wireless intra or inter body network protocol.

Example 87

A system comprising means for performing any one of the methods of any of examples 67-86.

Example 88

A non-transitory computer-readable storage medium comprising instructions that, when executed, cause at least one processor to any one of the methods of any of examples 67-86.

Example 89

A method for performing any of the operations described in this disclosure.

Example 90

A device or system comprising components configured to perform any of the operations described in this disclosure.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection may be considered a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transitory, tangible storage media. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A portable case for storing hearing assistance devices, the portable case comprising:
   at least one retention structure configured to retain at least part of a hearing assistance device;
   one or more communication units configured to exchange information between the portable case and one or more external devices;
   one or more input components configured to detect user inputs as part of a user interface, wherein the one or more input components comprise an inertial measurement component configured to detect user gestures performed while holding the portable case; and
   at least one processor configured to:
      detect when the at least part of the hearing assistance device is retained by the at least one retention structure; and
      responsive to receiving data, from the hearing assistance device, while the at least part of the hearing assistance device is retained by the at least one retention structure, cause the one or more communication units to communicate with the one or more external devices.

2. The portable case of claim 1, wherein the one or more external devices include: a computing device, the hearing assistance device, or at least one other hearing assistance device.

3. The portable case of claim 1, wherein the one or more communication units are configured for wireless communication between the portable case and the one or more external devices.

4. The portable case of claim 1, wherein the one or more communication units are configured for wired communication between the portable case and the one or more external devices.

5. The portable case of claim 1, wherein the one or more communication units are configured to communicate with the one or more external devices via at least one of: a near field communication radio, a Bluetooth® radio, a Wi-Fi® radio, a cellular radio, a software defined radio, a multi-modal radio, a near field magnetic induction radio, or a radio configured to communicate via a wireless intra or inter body-network protocol.

6. The portable case of claim 1, wherein the at least one processor is further configured to:
   receive, via the one or more communication units, first data from a first external device of the one or more external devices, the first data being encoded according to a first communication protocol;
   after decoding the first data, generate second data, the second data being encoded according to a second communication protocol; and
   send, via the one or more communication units, the second data to a second external device of the one or more external devices that is different than the first external device.

7. The portable case of claim 6, wherein:
   the hearing assistance device is a first hearing assistance device;
   the first external device is the first hearing assistance device; and the second external device is a second hearing assistance device.

8. The portable case of claim 6, wherein:
the hearing assistance device is a first hearing assistance device;
the first external device is the first hearing assistance device;
the second external device is a second hearing assistance device; and
the first communication protocol and the second communication protocol are a wireless intra or inter body network protocol.

9. The portable case of claim 6, wherein:
the first external device is the hearing assistance device;
the second external device is a mobile computing device;
the first communication protocol is a wireless intra or inter body network protocol; and
the second communication protocol is a second wireless communication protocol that is different than the wireless intra or inter body network protocol.

10. The portable case of claim 6, wherein the first data and the second data comprise audio data.

11. The portable case of claim 1, wherein the at least one processor is further configured to:
responsive to causing the one or more communication units to communicate with the one or more external devices, execute, based on information exchanged between the portable case and the one or more external devices, one or more operations on behalf of the one or more external devices.

12. The portable case of claim 1, further comprising a microphone, wherein the at least one processor is configured to wirelessly transmit audio captured using the microphone to the one or more external devices.

13. The portable case of claim 1, wherein the one or more input components comprise a microphone configured to detect voice commands.

14. The portable case of claim 1, wherein the one or more input components comprise a presence-sensitive input component configured to detect touch inputs.

15. The portable case of claim 1, further comprising:
one or more output components configured to generate outputs of a user interface, wherein the one or more output components comprise one or more of a display, a speaker, or a haptic feedback component configured to present the user interface.

16. The portable case of claim 1, further comprising:
a non-transitory computer-readable storage medium that stores at least one of:
instructions of one or more application programs that are executable by the at least one processor; or
user data accessed by the one or more application programs when executing at the at least one processor.

17. The portable case of claim 1, further comprising charging circuitry configured to charge an energy storage device of at least one of: the portable case or the hearing assistance device.

18. A method comprising:
detecting, by a portable case for storing hearing assistance devices, when at least part of a hearing assistance device is retained by at least one retention structure of the portable case;
receiving, by the portable case, from the hearing assistance device and while the at least part of the hearing assistance device is retained by the at least one retention structure, data;
responsive to receiving the data while the at least part of the hearing assistance device is retained by the at least one retention structure, communicating, by the portable case, using one or more communication units of the portable case and based on the data, with one or more external devices;
detecting, by an inertial measurement component of the portable case, user gestures; and
performing, by the portable case and based on the detected user gestures, an operation.

19. The method of claim 18, wherein the one or more external devices include: a computing device, the hearing assistance device, or at least one other hearing assistance device.

20. The method of claim 18, wherein communicating with the one or more external devices comprises communicating via at least one communication unit from the one or more communication units that includes a near field communication radio, a Bluetooth® radio, a Wi-Fi® radio, a cellular radio, a software defined radio, a multimodal radio, a near field magnetic induction radio, or a radio configured to communicate via a wireless intra or inter body-network protocol.

21. The method of claim 18, further comprising:
receiving, by the portable cases, via the one or more communication units, first data from a first external device of the one or more external devices, the first data being encoded according to a first communication protocol;
after decoding the first data, generating, by the portable case, second data, the second data being encoded according to a second communication protocol; and
sending, by the portable case, via the one or more communication units, the second data to a second external device of the one or more external devices that is different than the first external device.

22. The method of claim 18, further comprising:
responsive to causing the one or more communication units to communicate with the one or more external devices, executing, by the portable case, based on information exchanged between the portable case and the one or more external devices, one or more operations on behalf of the one or more external devices.

23. The method of claim 18, further comprising:
charging, by the portable case, via circuitry of the portable case, an energy storage device of at least one of: the portable case or the hearing assistance device.

24. A non-transitory computer-readable storage medium comprising instructions that, when executed by at least one processor of a portable case for storing hearing assistance devices, cause the at least one processor to:
detect when at least part of a hearing assistance device is retained by at least one retention structure of the portable case;
receive, from the hearing assistance device and while the at least part of the hearing assistance device is retained by the at least one retention structure, data;
responsive to receiving the data while the at least part of the hearing assistance device is retained by the at least one retention structure, communicate, using one or more communication units of the portable cases and based on the data, with one or more external devices;
detect, based on data generated by an inertial measurement component of the portable case, user gestures; and perform, based on the detected user gestures, an operation.

\* \* \* \* \*